US010047362B2

(12) United States Patent
Delaunay-Moisan et al.

(10) Patent No.: US 10,047,362 B2
(45) Date of Patent: Aug. 14, 2018

(54) LIGASE E3 RNF185 INHIBITORS AND USES THEREOF

(71) Applicant: COMMISSARIAT A L'ENERGIE ATOMIQUE ET AUX ENERGIES ALTERNATIVES, Paris (FR)

(72) Inventors: Agnès Delaunay-Moisan, Gif-sur-Yvette (FR); Michel Toledano, Boulogne-Billancourt (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/910,941

(22) PCT Filed: Aug. 5, 2014

(86) PCT No.: PCT/EP2014/066820
§ 371 (c)(1),
(2) Date: Feb. 8, 2016

(87) PCT Pub. No.: WO2015/018831
PCT Pub. Date: Feb. 12, 2015

(65) Prior Publication Data
US 2016/0194644 A1 Jul. 7, 2016

(30) Foreign Application Priority Data
Aug. 9, 2013 (EP) .................... 13306145

(51) Int. Cl.
C12N 15/00 (2006.01)
C07K 16/00 (2006.01)
A61K 31/00 (2006.01)
A61K 45/00 (2006.01)
C12N 15/113 (2010.01)
C07K 16/40 (2006.01)
A61K 31/7088 (2006.01)
(Continued)

(52) U.S. Cl.
CPC ...... *C12N 15/1137* (2013.01); *A61K 31/7088* (2013.01); *A61K 45/06* (2013.01); *C07K 16/40* (2013.01); *C12Q 1/6883* (2013.01); *C12N 2310/11* (2013.01); *C12N 2310/14* (2013.01); *C12N 2310/531* (2013.01); *C12N 2320/30* (2013.01); *C12N 2320/31* (2013.01); *C12Q 2600/136* (2013.01); *C12Q 2600/178* (2013.01)

(58) Field of Classification Search
CPC .............. C12N 15/1137; C12Q 1/6883; A61K 31/7088; A61K 45/06; C07K 16/40
See application file for complete search history.

(56) References Cited

FOREIGN PATENT DOCUMENTS

WO  WO 2008/008874      1/2008
WO  WO 2008008874 A2 *  1/2008

OTHER PUBLICATIONS

Origene catalog (Gene ID91445) (TG301946) human shRNA (see attached). Last Accessed Nov. 5, 2016.*
(Continued)

Primary Examiner — Cherie M Stanfield
(74) Attorney, Agent, or Firm — Saliwanchik, Lloyd & Eisenschenk

(57) ABSTRACT

The present invention relates to the use of an E3 ligase RNF185 inhibitor for treating cystic fibrosis and chronic obstructive pulmonary disease.

7 Claims, 8 Drawing Sheets

(51) Int. Cl.
A61K 45/06 (2006.01)
C12Q 1/6883 (2018.01)

(56) References Cited

OTHER PUBLICATIONS

Origene catalog RNF5 (Gene ID 6048) (TF18923) human shRNA (Jul. 2008). Last Accessed Nov. 5, 2016.*
Delaunay et al., (PLoS ONE. Feb. 2008;3(2):e1609; 15 pages).*
Tang et al., PLoS ONE. Sep. 2011;6(9):e24367;13 pages).*
Kuk et al., (Ther Adv Respir Dis. 2015;9(6):313-326).*
Ren et al., (Mol Biol Cell. Oct. 2013;24(19):3016-24. Epub Aug. 2013).*
Caohuy, H. et al., "Rescue of ΔF508-CFTR by the SGK1/Nedd4-2 Signaling Pathway," *Journal of Biological Chemistry*, Sep. 11, 2009, vol. 284, No. 37, pp. 25241-25253.
Caohuy, H., et al., "Supplementary Information for Rescue of ΔF508-CFTR by the SGK1/Nedd4-2 Signaling Pathway," *Journal of Biological Chemistry*, Sep. 11, 2009, vol. 284, No. 37, XP-002716980, pp. 1-8, retrieved from internet on Nov. 26, 2013: http://www.jbc.org/content/suppl/2009/07/17/M109.035345.DC1/jbc.M109.035345-1.pdf.
Eddins, M.J. et al., "Targeting the Ubiquitin E3 Ligase MuRF1 to Inhibit Muscle Atrophy," *Cell Biochemistry and Biophysics*, Mar. 30, 2011, vol. 60, No. 1-2, pp. 113-118.
El Khouri, E. et al., "RNF185 is a Novel E3 Ligase of Endoplasmic Reticulum-associated Degradation (ERAD) That Targets Cystic Fibrosis Transmembrane Conductance Regulator (CFTR)," *Journal of Biological Chemistry*, Oct. 25, 2013, vol. 288, No. 43, pp. 31177-31191 and supplemental material, pp. 1-8.
Fu, L. et al., "Dab2 is a key regulator of endocytosis and post-endocytic trafficking of the cystic fibrosis transmembrane conductance regulator," *Biochemical Journal*, Dec. 21, 2011, vol. 285, No. 2, pp. 633-643.
Tang, F. et al., "RNF185, a Novel Mitochondrial Ubiquitin E3 Ligase, Regulates Autophagy through Interaction with BNIP1," *PLOS ONE*, Sep. 9, 2011, vol. 6, No. 9, p. e24367 (1-13).
Written Opinion in International Application No. PCT/EP2014/066820, dated Oct. 13, 2014, pp. 1-7.
Shah, M. et al. "Inhibition of Siah2 ubiquitin by vitamin K3 (menadione) attenuates hypoxia and MAPK signaling and blocks melanoma tumorigenesis" *Pigment Cell Melanoma Res.*, Dec. 2009, pp. 1-21, vol. 22, No. 6, Supp. Info., p. 808, Supp. Figures and Tables, pp. 1-4.
Lee, K. et al. "Roles of 17-AAG-induced molecular chaperones and Rma1 E3 ubiquitin ligase in folding and degradation of Pendrin" *FEBS Letters*, 2012, pp. 2535-2541, vol. 586.
Zhou, Y. et al. "The E3 ligase RNF185 negatively regulates osteogenic differentiation by targeting Dvl2 for degradation" *Biochemical and Biophysical Research Communications*, 2014, pp. 431-436, vol. 447.

* cited by examiner

```
H.sapiens_RNF5     1 --------MAAAEEEDGG EGPNR---ERGGAGA TECN IC E TARE V 38
M.musculus_RNF5    1 --------MAAAEEEDGG EGPNR---ERGGASA TECN IC E TARE V 38
H.sapiens_RNF185   1 MASKGPSA SASPENSSAGG SGSSNGA SGGQDS ECN ICLDTAKD V 50
M.musculus_RNF185  1 MASKGPSA SASTENSNAGG SGSSN T SGGQDS ECN ICLDTAKD V 50
C.elegans_rnf-5    1 --------MASETKAPSEE TSSSN-----KDESAR ECN ICLDA KD  37
        Consensus    MASKGPSASASA+++E+GGP+GSSNG -GE+GG++ATFE(C)N I(C)LDTAKDAV H.sapiens_RNF5     39 V V CGHLY CWPCLHQWLE TR ERQ CPVCKAG ISRE KVV LYGRG SQKPQ 88
M.musculus_RNF5    39 V V CGHLY CWPCLHQWLE TR DRQ CPVCKAG ISRE KVV LYGRG SQKPQ 88
H.sapiens_RNF185   51 I LCGHLF CWPCLHQWLE TR PNRQ CPVCKAG ISRD KV I LYGRG STGQQ 100
M.musculus_RNF185  51 I LCGHLF CWPCLHQWLE TR PNRQ CPVCKAG ISRD KV I LYGRG STGQQ 100
C.elegans_rnf-5    38 V LCGHLF CWPCLS WLD TR NNQ CPVCK SA DGNKVV I YGRG D-SS 86
        Consensus    VSL(C)G(H)LF(C)WP(C)LHQWLETRPNRQV(C)PV(C)KAG ISR+KVVPLYGRGS+++Q H.sapiens_RNF5     89 DPR L KTPPRPQGQRPA ESR--------GFQ PF -DTGGFHF SFG V A -128
M.musculus_RNF5    89 DPR L KTPPRPQGQRPA ESR--------GFQ PF -DAGGFHF SFG V A -128
H.sapiens_RNF185   101 DPRE TPPRPQGQRPE ENR--------GFQG F FGDGGFQM SFG I A -141
M.musculus_RNF185  101 DPRE TPPRPQGQRPE ENR--------GFQG F FGDGGFQM SFG I A -141
C.elegans_rnf-5    87 DPR K V K NSE PPQSFAGFNWG DGGMM GGGPNVHF SFG I TV 136
        Consensus    DPR+KTPPRPQGQRPEPE+R--------GGFQ+FG FGDGGFHFSFG IGA- H.sapiens_RNF5     129 ----------------- PFGFF TTV NAHEPFRRG T ---------------149
M.musculus_RNF5    129 ----------------- PFGFF TTV NAHEPFRRG A ---------------149
H.sapiens_RNF185   142 ----------------- PF  IPATA N INDGRPPPA ---------------161
M.musculus_RNF185  142 ----------------- PF  IPATA N INDGRPPPA ---------------161
C.elegans_rnf-5    137 NGLFPLMFMLPF IQG I LSFVASF GNGNQGAAAA GGNGGGNDGNDGT 186
        Consensus    ------------------FPFGFFAT+FN++++++++AG---------------

H.sapiens_RNF5     150 ------------------ DLGQGHPASSWQDS LFLFLA IFFF FWLL SI 180
M.musculus_RNF5    150 ------------------ DLGQGHPASSWQDS LFLFLA IFFF FWLL SI 180
H.sapiens_RNF185   162 ------------------ PGTPQYVDEQFLSRL FL VALV IM FWLL IA 192
M.musculus_RNF185  162 ------------------ PGTPQYVDEQFLSRL FL VALV IM FWLL IA 192
C.elegans_rnf-5    187 HAHTHGHTHGPRGHGESAA GSRMAQEEEYLSN I KYIGFFML FV 235
        Consensus    ------------------VPG+++++++E++LS+LFLF+A+F+++FWLL++
```

FIGURE 1

A
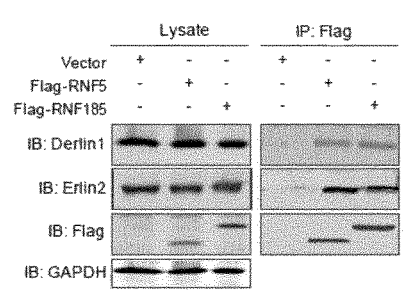
B
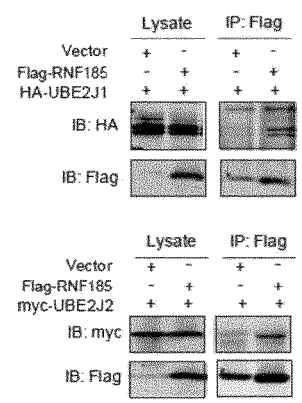
C
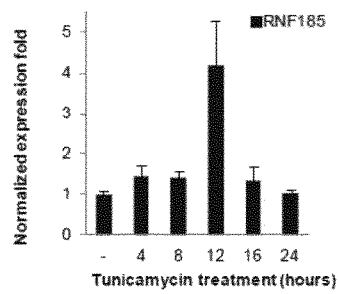
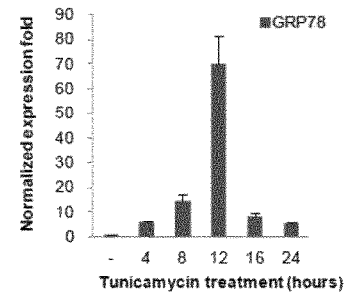
FIGURE 4

A
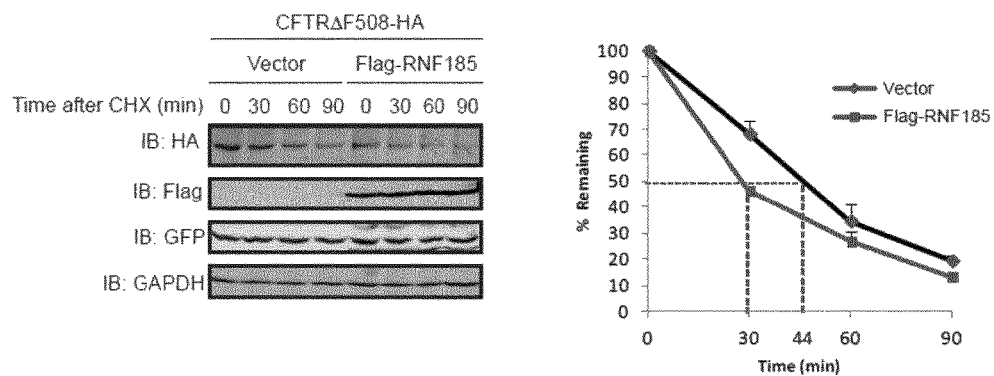
B
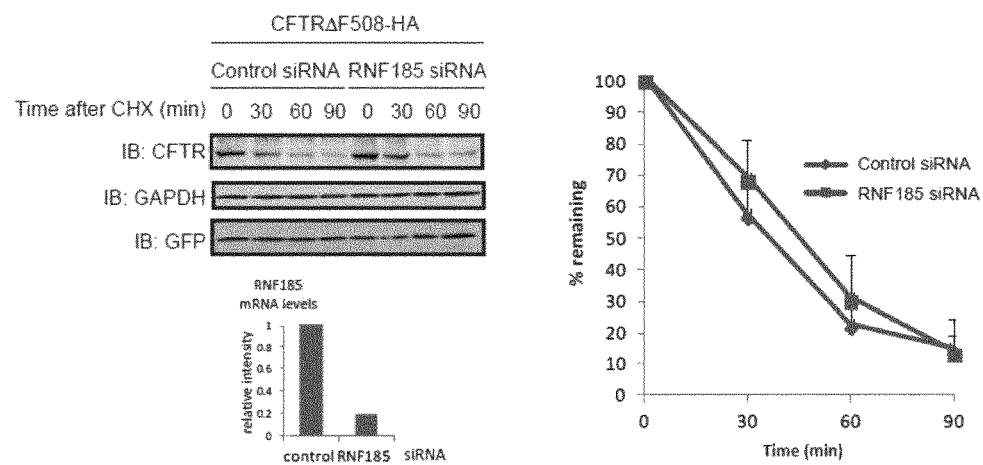
FIGURE 6

LIGASE E3 RNF185 INHIBITORS AND USES THEREOF

CROSS-REFERENCE TO RELATED APPLICATION

This application is the U.S. national stage application of International Patent Application No. PCT/EP2014/066820, filed Aug. 5, 2014.

The Sequence Listing for this application is labeled "Seq-List-replace.txt" which was created on Sep. 21, 2017 and is 18 KB. The entire content of the sequence listing is incorporated herein by reference in its entirety.

FIELD OF THE INVENTION

The present invention concerns inhibitors of E3 ligases targeting CFTR and uses thereof for treating cystic fibrosis and chronic obstructive pulmonary disease.

BACKGROUND OF THE INVENTION

Cystic fibrosis (CF) is an autosomal recessive genetic disease of the secretory glands that mainly affects the lungs, pancreas, intestine and liver. Cystic fibrosis, also known as mucoviscidosis, is the most common fatal recessive genetic disease in northern countries.

Cystic fibrosis is associated with mutations in the Cystic Fibrosis Transmembrane conductance Regulator (CFTR) gene, which encodes a cyclic-AMP dependent chloride channel at the apical membrane of epithelial cells. This channel mediates the transport of specific anions (e.g., chloride and thiocyanate) against their electrochemical gradient and hence acts to regulate the water content and the ionic composition of sweat, digestive juices and bronchial mucus.

The gene encoding CFTR has been identified and sequenced (See Gregory, R. J. et al. (1990) Nature 347:382-386; Rich, D. P. et al. (1990) Nature 347:358-362; Riordan, J. R. et al. (1989) Science 245:1066-1073).

Mutations affecting the function of the CFTR gene cause a major imbalance in ion and fluid transport across the epithelial cell membrane, most importantly at mucosal surfaces. In the lungs, the resulting decrease in chloride transport contributes to enhanced mucus dehydration and defects in mucocilliary clearance, leading to mucus accumulation, bacterial colonization and inflammation. This results in recurrent respiratory tract microbial infections that are the primary cause for morbidity and mortality in cystic fibrosis patients. CFTR loss-of-function also causes imbalances in ion and fluid transport in other major exocrine glands. Consequently, CF patients suffer from gastrointestinal symptoms and pancreatic insufficiency that have to be compensated for by a proper diet and can also, if left untreated, result in death. The majority of males with CF are infertile and fertility is decreased among CF females.

Sequence analysis of the CFTR gene of CF patients' chromosomes has revealed a variety of disease-causing mutations. To date, more than 1000 disease-causing mutations in the CFTR gene have been identified. The most common CFTR mutant (in about 70% of CF patients) consists of the deletion of phenylalanine at position 508. The deletion of residue 508 in $\Delta$F508-CFTR induces major folding defects that primarily result in the inability of the CFTR$\Delta$F508 protein to reach its proper location at the plasma membrane due both to increased endoplasmic reticulum (ER) retention and ER-associated degradation (ERAD) by the ubiquitin-proteasome machinery. The marginal targeting of the partially functional $\Delta$F508-CFTR protein at the plasma membrane is not sufficient functional and therefore assimilates to a loss of function. Artificially increasing the number of CFTR channels targeted to the membrane showed that CFTR$\Delta$F508 remains partially functional although the $\Delta$F508 mutation exhibits an intrinsic channel gating defect and accrued protein turnover at the plasma membrane. The folding defects of CFTR imposed by the $\Delta$F508 mutation drastically reduce the number of functional channels reaching the apical membrane and thereby anion and fluid transport across epithelia (Ward and Kopito, 1994, J. Biol. Chem. 269, 25710-25718; Ward and Kopito, 1995, Cell 83, 121-127; Lukacs et al., 1994, EMBO J. 13, 6076-6086; J. R. Riordan, Am. J. Hum. Genet. 1999 June, 64(6):1499-1504. PMCID: PMC1377893).

Cystic fibrosis mutations impact CFTR function through different mechanisms that must be considered when designing therapeutic strategies. Class II mutations (in 88% of CF patients) include the above-mentioned most prevalent mutation, CFTR$\Delta$F508; these mutations prevent ER folding of CFTR, and hence its trafficking in the secretory pathway, and trigger degradation of the mutant proteins by ERAD.

Both gene therapy and pharmacotherapy have been proposed as ways to restore CFTR function, but these are currently lacking for class II mutants.

Treatment directed at class II mutations aims at increasing the amount of proteins at the plasma membrane by correcting their trafficking defect. CFTR$\Delta$F508 also displays reduced channel opening and increased turnover when forced at the plasma membrane. Therefore, efficient restoration of CFTR-class II mutation function might also require molecules aimed at correcting the gating defects of these mutations and at increasing plasma membrane stability, in addition to the interventions aimed at increasing protein plasma membrane expression. Such molecules are already available (VX-770 and VX-809, respectively) (Van Goor et al., PNAS 2009; Van Goor et al., PNAS 2011). Compounds aimed at restoring CFTR trafficking are defined as "correctors", those improving the channel opening are named as "potentiators", and a combined therapy including correctors and potentiators is currently considered for CFTR$\Delta$F508 patients. Correctors can be separated into two classes: those that bind to CFTR molecules and act on its folding rate and stability, and are therefore named "pharmacological chaperones", and those that act on the proteostasis network, i.e., that target proteins that regulate CFTR folding, degradation and/or vesicular trafficking (proteostasis regulators (PR)). However, currently identified correctors remain poorly effective on their own and their mode of action and CFTR specificity remain poorly defined. Recent trends points to the use of a combination of correctors that target CFTR folding defects occurring during biosynthesis to enhance CFTR maturation and plasma membrane expression (Okiyoneda and Lukacs (2013) Nature Chem. Biol.).

Inhibition of the Endoplasmic-Reticulum-Associated Degradation (ERAD) machinery promotes CFTR stabilization in the endoplasmic reticulum (ER); components of ERAD have been proposed to be relevant PR targets in CF treatment (Younger et al. (2006) Cell 126, 571-582; Younger et al. (2004) J. Cell. Biol. 167, 1075-1085). Inhibition of ERAD is already considered beneficial by increasing the amount of mutant CFTR made available to chemical chaperones, if not by enhancing CFTR plasma membrane expression.

General ERAD inhibition as performed by proteosomal inhibition is not well-suited, as it results in the accumulation of insoluble ubiquitinated aggregates, hampering further export of the protein out of the ER.

E3 ligases are central components of the ERAD machinery, tagging ERAD substrates for subsequent degradation by the proteasome. ERAD E3 ligases are targets that are considered suitable to inhibit CFTR degradation, as: i) their inhibition is believed to stabilize ERAD substrates in a soluble state; ii) they are relatively substrate-specific; and iii) their function should be conserved in many cell types. E3 ligases' specificity is dictated by their association with specific chaperones that operate by recruiting the E3 ligases to their specific substrates. Identification of these chaperones and of their interaction interfaces should help define drug target domains in ligases to further increase specificity. The development of efficient E3 ligase inhibitors has been validated as a therapeutic strategy in CF.

So far, two E3 ligases, RNF5 and CHIP, have been associated with the ER degradation of CFTR proteins, more specifically CFTRΔF508. Inactivation of RNF5 or CHIP promotes the stabilization of the mutant protein in a foldable state and an increased maturation of the mutant protein when cells are co-treated with a pharmacological chaperone (e.g., the Corr-4a corrector). In this specific case, Corr-4a and RNF5 depletion target distinct checkpoints of the CFTR quality control; RNF5 targets the first checkpoint, which occurs during CFTR synthesis. RNF5 is thought of as a major target for increasing the amount of foldable CFTR proteins (Younger et al. (2006) Cell 126, 571-582; Grove et al. (2009) Mol. Biol. Cell 20, 4059-4069).

There is at present no efficient cure for cystic fibrosis. Current treatments are only palliative: they include antibiotic cures (for lung infections), chest physiotherapy/mechanical expectoration (for mucus accumulation), surgery and mechanical ventilation. Hence there is a strong need for the development of new therapies for the treatment of cystic fibrosis.

SUMMARY OF THE INVENTION

The present invention identifies a component of the ERAD machinery as a novel target in the treatment of cystic fibrosis or chronic obstructive pulmonary disease (COPD). More particularly, the invention relates to a new E3 ligase named RNF185 that targets both CFTR wild-type and CFTRΔF508, and to inhibitors thereof for use in restoring CFTRΔF508 function. A combined inhibition of RNF185 and RNF5 potently and surprisingly inhibits the ER degradation of CFTRΔF508 with a synergistic effect.

It is therefore an object of the present invention to provide an E3 ligase RNF185 inhibitor for use in the treatment of cystic fibrosis or COPD.

In a particular embodiment, the E3 ligase RNF185 inhibitor acts through direct binding to E3 ligase RNF185. In a particular embodiment, said E3 ligase RNF185 inhibitor additionally binds directly to E3 ligase RNF5, so that said E3 ligase is simultaneously inhibited.

In a preferred embodiment, the E3 ligase RNF185 inhibitor is used in combination with an E3 ligase RNF5 inhibitor.

In a particular embodiment, said inhibitor is selected from the group consisting of a small molecule, an anti-E3 ligase antibody, and a nucleic acid inhibiting or decreasing the expression of E3 ligase. In a preferred embodiment, the nucleic acid is selected from the group consisting of an antisense nucleic acid, a ribozyme and an interfering RNA, preferably an siRNA or an shRNA.

In a particular embodiment, the E3 ligase RNF185 inhibitor inhibits the expression of E3 ligase RNF185. In this regard, said inhibitor is an interfering RNA, preferably an siRNA or an shRNA.

The present invention further relates to a product comprising: (a) an E3 ligase RNF185 inhibitor; and (b) an E3 ligase RNF5 inhibitor, as a combined preparation for simultaneous, separate or sequential use as a medicament. Preferably, the present invention also relates to a product for use in the treatment of cystic fibrosis and/or chronic obstructive pulmonary disease.

Preferably, cystic fibrosis is associated with Class II mutations (i.e., CFTRΔF508).

The invention also relates to a pharmaceutical composition comprising an E3 ligase RNF185 inhibitor and an E3 ligase RNF5 inhibitor. Preferably, the E3 ligase inhibitor is selected from a small molecule, an antibody and a nucleic acid inhibiting or decreasing the expression of E3 ligase, preferably an siRNA or an shRNA.

According to the invention, the composition may further comprise at least one another active compound. In a particular embodiment, the pharmaceutical composition further comprises a corrector aimed at restoring CFTR trafficking, such as another E3 ligase inhibitor, preferably a corrector from the pharmacological chaperone class (e.g., VX-809), a potentiator improving the channel opening and/or a molecule preventing or interfering with the chaperones' recruitment.

A further object of the invention relates to a method of screening for or identifying compounds useful for the treatment of cystic fibrosis or chronic obstructive pulmonary disease, comprising:

a) Providing or obtaining a candidate compound;
b) Determining whether said candidate compound inhibits the activity of an E3 ligase RNF185; and
c) Selecting said candidate compound if it inhibits the activity of an E3 ligase RNF185.

In one embodiment, the screening method may further comprise determining whether said selected candidate compound inhibits the activity of an E3 ligase RNF5, and selecting said candidate compound if it inhibits the activity of an E3 ligase RNF5. Optionally, the inhibition of the activity is an inhibition or decrease of the expression.

These and the other objects and embodiments of the invention will become more apparent after the detailed description of the invention.

BRIEF DESCRIPTION OF THE FIGURES

FIG. 1. RNF185 is an RNF5 homolog conserved in higher eukaryotes. Amino acid sequence alignment of human (GI: 45708382) and mouse (GI: 15928691) RNF185 with their human (GI: 5902054), mouse (GI: 9507059) and *C. elegans* RNF5 (GI: 3874385) homologs. The two C-terminal membrane domains are underlined. The seven cysteine residues and the histidine residue constitutive of the RING domain are circled. *H. sapiens*_RNF5, SEQ ID NO: 39; *M. musculus*_RNF5. SEQ ID NO: 38, *H. sapiens*_RNF185, SEQ ID NO: 41; *M. musculus*_RNF185, SEQ ID NO: 42; *C. elegans*_RNF5, SEQ ID NO: 40; Consensus sequence, SEQ ID NO: 45.

A. Expression of RNF185 in mouse tissues. Total RNAs were purified from WT mouse tissues and were retrotranscribed for quantitative-PCR analysis using RNF185-specific primers. Ppia1 and RN18S were used as references. Analysis was carried out on RNA samples extracted from tissues of three different mice. B. RNF185 can auto-ubiquitinate. Purified GST, GST-RNF185 and GST-RNF5 were incubated at 37° C. in the presence of ATP, ubiquitin, E1 and three different E2 enzymes. The reaction was next subjected to immunoblotting (IB) with anti-GST or anti-ubiquitin antibodies. C. Schematic representation of the RNF185 constructs used in this study. RNF185 WT: Wild-type RNF185; RNF185 ΔC: RNF185 with truncation of the most distal transmembrane domain; RNF185 RM: RNF185 with two punctual mutations in the RING domain; RNF185 ΔR: RNF185 mutant with total deletion of the RING domain. D. RNF185 ubiquitin ligase activity is dependent on the RING domain. GST-RNF185 WT and its RING mutant counterparts were processed as in B.

Figure 3:
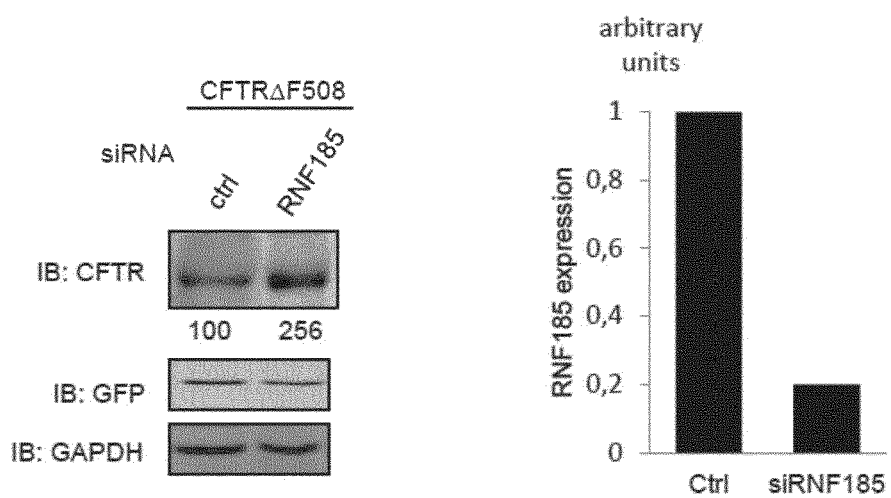

FIG. 3. Downregulation of RNF185 increases CFTR levels in HEK293 cells stably expressing CFTRΔF508.

Cells stably expressing CFTRΔF508 were co-transfected with siRNAs directed against a non-specific sequence or against RNF185 and GFP plasmid tracer. 48 hours later, the cells were lysed and equal amounts of protein extracts were loaded on reducing SDS-PAGE for immunoblot with the indicated antibodies (left panel). GFP was used to monitor transfection efficiency and GAPDH was used as a loading control. RNF185 extinction was controlled by Q-PCR analysis (right panel).

FIG. 4. RNF185 interacts with ERAD components and is induced by UPR.

A. RNF185 interacts with Derlin-1 and Erlin2. HEK293T cells were transfected with the control vector, Flag-RNF185 or Flag RNF5 (0.5 μg of plasmid per well of a 6-well plate). 24 hours post-transfection, cells were lysed and co-immunoprecipitation was performed using Flag antibody. Immunoprecipitated proteins were loaded on reducing 14% SDS-PAGE and immunoblotted with antibodies against endogenous Derlin-1, endogenous Erlin2 or Flag. B. RNF185 interacts with both enzymes of the Ubc6 family. HEK293T cells were transfected with the control vector or Flag-RNF185 together with a plasmid expressing HA-UBE2J1 or myc-UBE2J2. Cells were then processed as in A. In this experiment, Flag-RNF185 co-migrates with the antibody light chain as seen in the control lane (*). C. RNF185 expression is increased after tunicamycin treatment. HEK293 cells were treated with 2 μg/ml of tunicamycin during the indicated times. Total RNAs were extracted and retrotranscribed. Quantitative-PCR analysis was performed using RNF185-specific primers and its expression levels were normalized to GAPDH levels (left panel). Results are shown as the mean of three independent experiments. Change in GRP78 expression was used as a control for UPR induction by tunicamycin (right panel).

Figure 5:
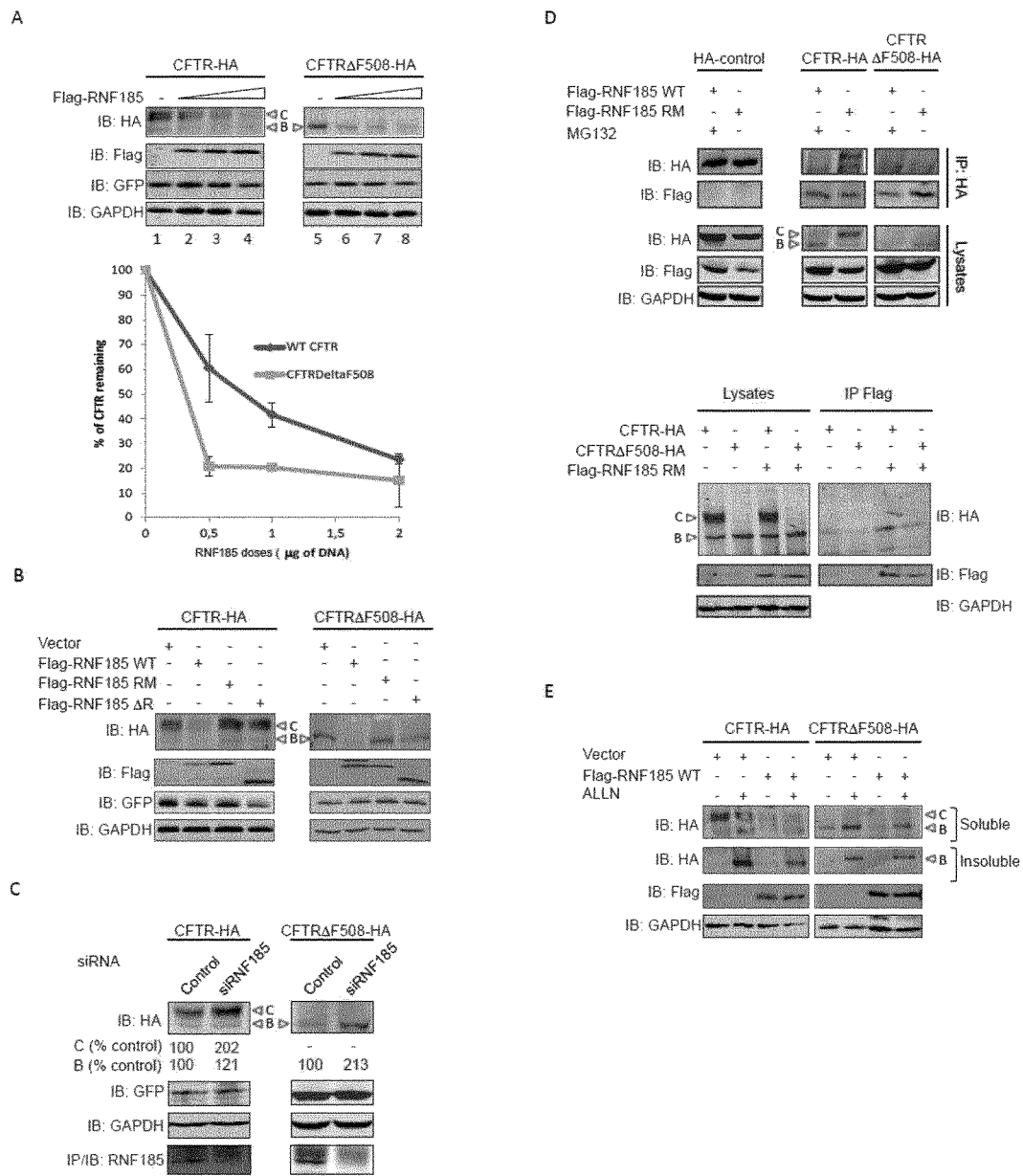

FIG. 5. RNF185 induces the ubiquitin-proteasome-dependent degradation of CFTR proteins.

A. RNF185 overexpression decreases the steady state levels of WT CFTR and CFTRΔF508. Cells were co-transfected with control vector or increasing amounts of Flag-RNF185 (0.5, 1 or 2 μg per well) and CFTR-HA or CFTRΔF508-HA. A low amount (0.1 μg per well) of a GFP-expressing plasmid was co-transfected in each condition and the monitoring of GFP expression was used as a control for transfection efficiency. 24 hours post-transfection, cells were lysed and equal amounts of protein extracts were loaded on reducing SDS-PAGE for immunoblot (IB) with the indicated antibodies. GAPDH was used as a loading control. The core glycosylated immature form and the mature glycosylated form of CFTR are denoted B and C, respectively. Steady state levels of CFTR and CFTRΔF508 were quantified using ImageJ software and were normalized to GAPDH and GFP levels. Results from three independent experiments have been plotted and are expressed as a percentage of the control (vector) condition. B. Decrease in CFTR levels is dependent on RNF185 E3 ligase activity. Cells were co-transfected with control vector or vectors expressing RNF185 WT, RNF185 RM or RNF185 ΔR together with CFTR-HA or CFTRΔF508-HA. As in A, co-transfection with a GFP-expressing plasmid was used to monitor transfection efficiency. Cells were next processed as in A. C. RNF185 knockdown increases CFTR levels. Cells were co-transfected with CFTR-HA or CFTRΔF508-HA together with a control or an RNF185-specific siRNA. 48 hours later the cells were processed as described in A. RNF185 extinction was monitored after immunoprecipitation of the cellular extracts with anti-RNF185 antibody. Relative steady state levels of CFTR proteins were quantified using ImageJ software. Results are expressed as a percentage of the control condition. D. RNF185 interacts with CFTR and CFTRΔF508. HEK293T cells were co-transfected with the indicated plasmids. HA-H3, a plasmid expressing HA-tagged histone H3, was used as a negative control for immunoprecipitation (upper panel). Cells expressing WT RNF185 were treated with MG132 during 5 hours before processing with the lysis. Co-immunoprecipitations were carried out with equal amounts of cell lysates using anti-HA antibody (upper panel) or anti-Flag antibody (lower panel). The immunoprecipitates were next immunoblotted with the indicated antibodies. E. Proteasome inhibition rescues RNF185-induced decrease in CFTR levels. HEK293 cells were co-transfected with the indicated plasmids and treated with ALLN or DMSO for 12 hours, 24 hours post-transfection. After cell lysis, the detergent insoluble and soluble fractions were subjected to immunoblot analysis with the indicated antibodies.

FIG. 6. Analysis of CFTRΔF508 degradation by cycloheximide chase.

A. Cycloheximide (CHX) chase analysis of CFTRΔF508 upon RNF185 expression. HEK293T cells were co-transfected with CFTRΔF508-HA together with a control vector or vector expressing RNF185 WT. A GFP-expressing plasmid was co-transfected as a marker for transfection efficiency. 24 hours later, protein extracts were prepared at the indicated time points after cycloheximide treatment (100 μg/mL) and loaded onto reducing SDS-PAGE. Immunoblotting was performed with the indicated antibodies. Relative changes in the half-life of CFTRΔF508 were quantified from three different experiments using ImageJ software and normalized to GAPDH and GFP levels. The obtained values were plotted against time. B. Cycloheximide (CHX) chase analysis of CFTRΔF508 upon RNF185 knockdown. Cells stably expressing CFTRΔF508-HA were transfected with a control or an RNF185-directed siRNA. 48 hours later, cells were treated with CHX and processed as in A. Downregulation of RNF185 expression was controlled by Q-PCR (inset right panel).

Figure 7:
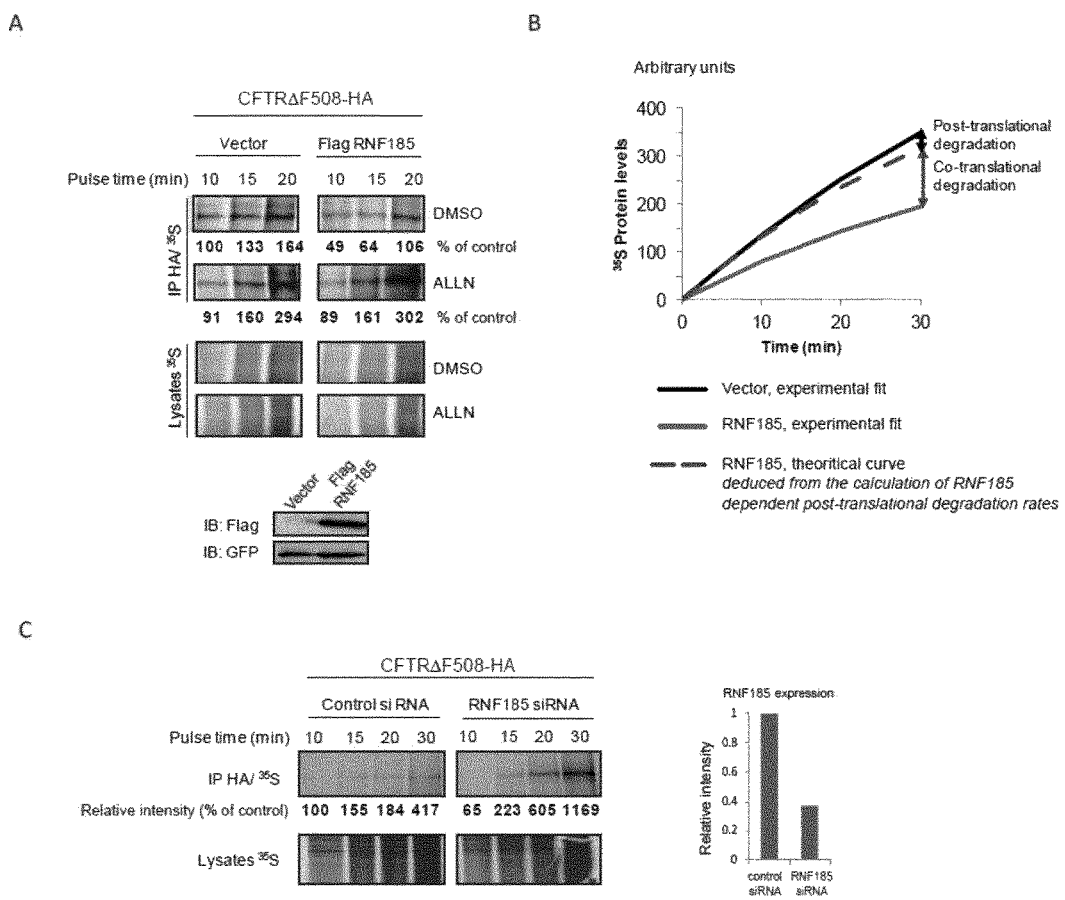

FIG. 7. RNF185 targets CFTRΔF508 to co-translational degradation.

A. Measure of CFTRΔF508 labeling rates upon RNF185 over-expression. Cells were co-transfected with CFTRΔF508-HA together with RNF185 or the corresponding control vector. 24 hours later, the cells were labeled with $^{35}S$ Met/Cys radiolabeling mix and the synthesis of $^{35}S$-labeled CFTRΔF508 protein was monitored over time by immune-precipitating equal amounts of the labeled extracts with anti-HA antibody. ALLN or DMSO was added in the medium 1h30 before labeling. Consistency of $^{35}S$-labeling between samples was controlled by loading the supernatants of the corresponding immunoprecipitation (depicted as lysates $^{35}$S). Quantification of the experiment was performed using ImageJ software and the intensity of labeled CFTR was normalized to the total amount of radioactivity initially present in the corresponding lysate. Results are expressed as a percentage of the vector condition quantified at 10 minutes in DMSO. RNF185 expression was confirmed by SDS-PAGE analysis (lower panel). B. Comparison of the experimental fitted curves (solid lines), accounting for the observed accumulation of $^{35}$S-labeled CFTRΔF508 over time in the absence and presence of RNF185, with the theoretical curve (dashed line) predicting the accumulation of $^{35}$S-labeled CFTRΔF508 if RNF185 only impacted the CFTR post-translational degradation rate. The theoretical RNF185 curve was obtained by setting equal the rate of synthesis in the presence or absence of RNF185. C. Measure of CFTRΔF508 labeling rates upon RNF185 knockdown. Cells stably expressing CFTRΔF508 were transfected using control or RNF185-directed siRNA. 48 hours after transfection, the cells were labeled and processed as in A. Efficiency of RNF185 knockdown was controlled by Q-PCR analysis (right panel).

Figure 8A:
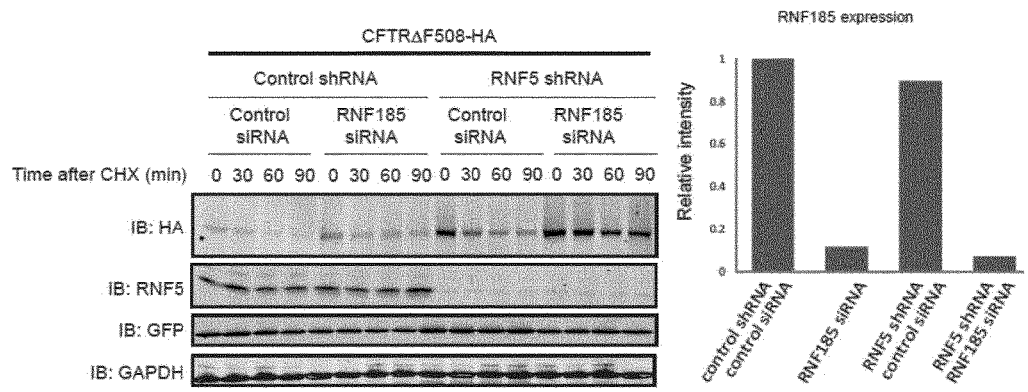

FIG. 8. Combined depletion of RNF185 and RNF5 synergistically blocks CFTRΔF508 degradation.

A. Analysis of CFTRΔF508 turnover upon combined RNF185 and RNF5 knockdown. HEK293 cells stably expressing a control shRNA or an shRNA sequence targeting RNF5 were co-transfected with CFTRΔF508-HA together with a control siRNA or an siRNA sequence targeting RNF185. 48 hours later, the cells were treated with CHX for the indicated times and processed as in FIG. 6A. Immunoblotting following SDS-PAGE was performed using the indicated antibodies. Downregulation of RNF185 expression was controlled by Q-PCR (right panel). B. Relative changes in the half-life of CFTRΔF508 were quantified from three independent experiments using ImageJ software and normalized to GAPDH and GFP levels. The obtained values were plotted against time. The left panel depicts relative values normalized to the control condition (control shRNA, control siRNA), where initial CFTRΔF508 levels in this condition have been artificially normalized to 1. The right panel depicts CFTRΔF508 intrinsic half-life after translation block, the initial time point for each condition being set at 100%.

Figure 9:
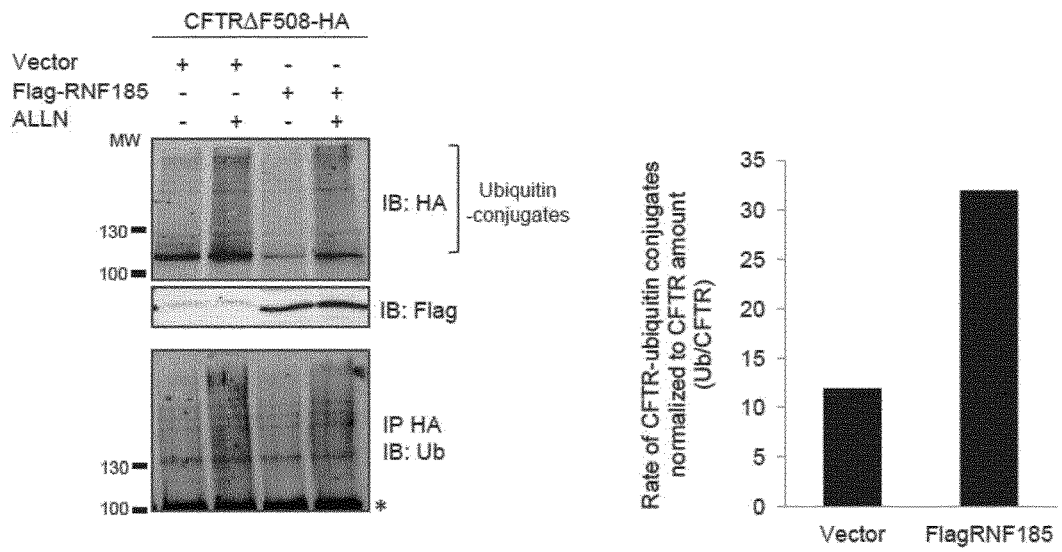

FIG. 9. In vivo ubiquitination of CFTR proteins.

Cells were co-transfected with CFTRΔF508-HA and flag-RNF185 or the corresponding empty vector. 24 hours later, cells were washed and lysed in the presence of 5 mM NEM. When mentioned, ALLN was added 4 hours before lysis. The resulting extracts were loaded on SDS-PAGE to perform the indicated immunoblottings (left panel). CFTRΔF508 protein and its corresponding ubiquitin conjugates were quantified using ImageJ software and their ratio is reported in the right panel.

Figure 10:
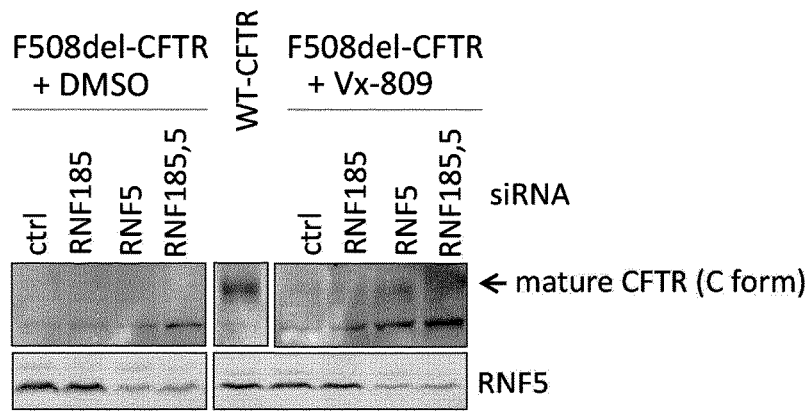

FIG. 10. Knockdown of RNF5 and RNF185 synergizes with Vx-809 treatment to restore CFTR maturation.

HEK293 cells stably expressing control or RNF5-targeted shRNA were transfected with F508del-CFTR expressing vector together with control or RNF185-targeted siRNA. 24 h after transfection, cells were further incubated with 5 μM of Vx-809 or DMSO for another 24 hours. 48 hours after initial transfection, cells were harvested and lysates probed by Western blot to monitor CFTR levels and maturation. RNF5 knockdown is validated by Western blot. RF185 knockdown is validated by Q-PCR.

Figure 11:
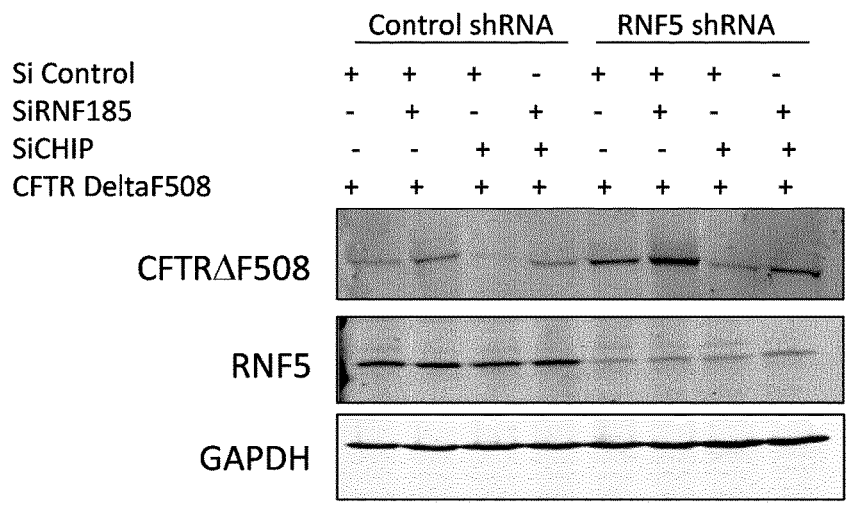

FIG. 11. CHIP knockdown does not further stabilize F508del-CFTR in RNF5/RNF185 double knockdown cells. CHIP was previously reported as an E3 ligase targeting CFTR to ERAD. The inventors tested the impact on CFTR levels of combining the down-regulation of these different E3 ligases. DelF508-CFTR levels were measured after E3 ligase knockdown (simple and combination). RNF5 knockdown is validated by Western blot. RF185 and CHIP knockdown is validated by Q-PCR.

DETAILED DESCRIPTION OF THE INVENTION

The inventors showed that RNF185, a RING domain-containing polypeptide homologous to RNF5, controls the stability of CFTR and of the CFTRΔF508 mutant in a RING and proteasome-dependent manner, and that RNF185 silencing stabilizes CFTR proteins. Turnover analyses indicate that, as RNF5, RNF185 target CFTR to co-translational degradation. Furthermore, the inventors showed, in a surprising way, that simultaneous depletion of RNF5 and RNF185 profoundly blocks CFTRΔF508 degradation not only during translation, but also after synthesis is complete. Accordingly, the inventors identified RNF185 and RNF5 as a novel E3 ligase module that is central to the control of CFTR degradation.

The following is a description of the present invention, including preferred embodiments thereof given in general terms. The present invention is further exemplified in the disclosure given under the heading "Examples" hereinbelow, which provides experimental data supporting the invention and means of performing the invention.

Definitions

The present disclosure will be best understood by reference to the following definitions.

As used herein, the term "E3 ligase inhibitor" refers to any molecule able to decrease or inhibit the expression and/or activity of the E3 ligase of interest according to the invention. Preferably, such a ligase inhibitor is a direct inhibitor, meaning that it interacts directly with either the E3 ligase protein or a nucleic acid encoding said ligase. The E3 ligase inhibitors according to the invention are capable of inhibiting or decreasing the functional activity of the ligase in vivo and/or in vitro. The inhibitor may inhibit the functional activity of the E3 ligase by at least about 30%, preferably by at least about 50%, preferably by at least about 70, 75 or 80%, still preferably by 85, 90, 95, or 100%. In particular, the inhibitor may inhibit the E3 ligase expression by at least about 10%, preferably by at least about 30%, preferably by at least about 50%, preferably by at least about 70, 75 or 80%, still preferably by 85, 90, 95, or 100%.

In the following "E3 ligase X inhibitor" and "X inhibitor" are used indifferently to refer to an inhibitor of the E3 ligase X. For instance, both E3 ligase RNF185 inhibitor and RNF185 inhibitor refer to an inhibitor of E3 ligase RNF185. Similarly, both E3 ligase RNF5 inhibitor and RNF5 inhibitor refer to an inhibitor of E3 ligase RNF5.

RNF185 refers to human Ring Finger Protein 185 (RNF185). The reference entries for human RNF185 are the following: UniGene Hs. 517553, GeneCard Identifier GCID GC22P031566, HGNC ID: 26783, and UniProtKB: Q96GF1. Reference sequences for the amino acid sequences in Genbank are NP_689480.2 (Isoform 1) and NP_001129297.1 (Isoform 2), the first one being predominant. Reference sequences for the mRNA sequences in Genbank are NM_152267.3 and NM_001135825.1, respectively. Aliases of RNF185 are the following: E3 Ubiquitin-Protein Ligase RNF185, BSK65-TEST1, FLJ38628, BSK65-TEST2, BSK65-MONO1, BSK65-TEST3, BSK65-MONO2, BSK65-PANC1, EC 6.3.2., and BSK65-PANC2.

RNF5 refers to human Ring Finger Protein 5, E3 ubiquitin protein ligase (RNF5). The reference entries for human RNF5 are the following: UniGene Hs. 731774, GeneCard Identifier GCID GC06P032146, HGNC ID: 10068, and UniProtKB: Q99942. The reference sequences for the amino acid sequences in Genbank are NP_008844.1. The reference sequences for the mRNA sequences in Genbank are NM_006913.3. Aliases of RNF5 are the following: Protein G16, RMA1, Ram1 Homolog, RINGS, E3 Ubiquitin-Protein Ligase RNF5, G16, EC 6.3.2. NG2, HsRma1, and RING Finger Protein 5.

Within the context of the invention, the term "treatment" denotes curative, symptomatic, and preventive treatment. As used herein, the term "treatment" of a disease refers to any act intended to extend the lifespan of patients, such as therapy and retardation of disease progression. The treatment can be designed to eradicate the disease, to stop the progression of the disease, and/or to promote the regression of the disease. The term "treatment" of a disease also refers to any act intended to decrease the symptoms associated with the disease. The patient to treat is any mammal, preferably a human being.

E3 Ligase RNF185 Inhibitor as a Therapeutic Agent in Cystic Fibrosis and/or Chronic Obstructive Pulmonary Disease The inventors have herein identified a novel ER-associated E3 ligase of ERAD, named E3 ligase RNF185, that is homologous by sequence to RNF5. Interestingly, RNF185 specifically targets CFTR and CFTRΔF508 to proteasomal degradation. As RNF5, RNF185 controls CFTR stability during translation and combined inactivation of RNF185 and RNF5 lead to a dramatic stabilization of CFTRΔF508. Surprisingly, the inventors have identified that the combination of inhibitors of E3 ligase RNF185 and E3 ligase RNF5 provides a synergistic effect on the inhibition of the ER degradation of CFTRΔF508. Indeed, the inventors have shown that such combination is aimed at reinforcing the desired effects. More particularly, the inventors have shown that RNF185 can target mutant CFTRΔF508 to co-translational degradation, i.e., during CFTR protein synthesis. Furthermore, simultaneous inhibition of RNF185 and RNF5 results in a profound stabilization of CFTRΔF508, much greater than that obtained following single depletion of RNF5 or RNF185. Surprisingly, the inventors discovered that such stabilization is not only due to the function of RNF5 and RNF185 in CFTR co-translational quality control, but also to their redundant function in regulating CFTR post-translational turnover rates.

Accordingly, in a first aspect, the present invention provides new therapeutic agents for treating cystic fibrosis or COPD, namely the E3 ligase RNF185 inhibitors. Preferably, the E3 ligase RNF185 inhibitor is used in combination with an RNF5 inhibitor.

Indeed, by conducting experiments, the inventors have discovered that an E3 ligase RNF185 inhibitor may be useful not only for treating cystic fibrosis but also chronic obstructive pulmonary disease (COPD).

chronic obstructive pulmonary disease is a disease characterized by a persistent obstruction of the respiratory tract involving mucus stasis, inflammation and remnant infection (chronic bronchitis). Tobacco smoke is the major contributor to COPD. COPD shares some pathological features with cystic fibrosis, including mucus stasis, which has been shown to contribute to the decline of lung function and increased mortality (Rogers, COPD, 2005; Vestbo, J. 2002).

Recent studies point to a possible role of CFTR dysfunction in COPD pathophysiology. These showed that CFTR function is decreased in response to cigarette smoke exposure (CSE), through a mechanism decreasing its availability at the plasma membrane (Sloane, P. A. et al., Plos One 2012; Clunes et al., FASEB, Vol. 26, 2012). CSE also causes a reduction of CFTR function in the upper airways of healthy and COPD smokers (Cantin, A. M. et al., Am. J. Respir. Crit. Care Med., 2006; Sloane, P. A. et al., 2012). CFTR functional decrease induced by CSE can be reversed by increasing the channel activity through the action of potentiator molecules that increase the activity of CFTR proteins reaching the plasma membrane (Sloane, P. A. et al., 2012).

A parallel study shows that RNF5/RMA1 expression is elevated in COPD patients with emphysema through an unknown mechanism (Min et al., J. Mol. Med., 2011). Such increase could contribute to exaggerate CFTR loss of function.

Given the involvement of CFTR loss of function in COPD and the elevation of RNF5 levels monitored in COPD patients, the inventors proposed to use E3 ligase inhibitors, and more particularly RNF185 inhibitors, and still preferably a combination of RNF185 and RNF5 inhibitors, to stimulate CFTR function by increasing the amount of CFTR reaching the plasma membrane.

Accordingly, it is an object of the invention to provide an E3 ligase RNF185 inhibitor for use in the treatment of cystic fibrosis and/or chronic obstructive pulmonary disease.

The invention further provides a method of treatment of cystic fibrosis and/or COPD in a patient in need thereof, wherein a pharmaceutically effective amount of E3 ligase RNF185 inhibitor is administered to the patient. It also relates to the use of an E3 ligase RNF185 inhibitor for the manufacture of a medicament for the treatment of cystic fibrosis and/or COPD.

In one embodiment, the E3 ligase RNF185 inhibitor may act through direct binding to E3 ligase RNF185. By direct binding is intended the binding to the protein, and also the mRNA encoding the protein. Preferably, the direct binding is a binding to E3 ligase RNF185 mRNA.

In a particular embodiment of the invention, said E3 ligase RNF185 inhibitor is able to inhibit the expression and/or activities of said E3 ligase RNF185. Optionally, said inhibitor is in addition capable of inhibiting other E3 ligases of interest. In a preferred embodiment, the E3 ligase RNF185 inhibitors of the invention also exhibit a capacity for inhibiting E3 ligase RNF5.

An E3 ligase RNF185 inhibitor of the invention may act by blocking and/or inhibiting the activity of the E3 ligase RNF185 of interest. This may, for example, be achieved by inhibiting the activity of the E3 ligase RNF185. Functional activity of the E3 ligase RNF185 may be readily assessed by the one skilled in the art according to known methods (Seth J. Goldenberg, Jeffrey G. Marblestone, Michael R. Mattern, and Benjamin Nicholson, Biochem. Soc. Trans., 2010 February, 38(Pt 1):132-136; Sun, Y., Methods Enzymol., 2005, 399:654-63).

The E3 ligase RNF185 inhibitor of the invention may also act by blocking and/or inhibiting the expression of the E3 ligase RNF185. The decrease or inhibition of E3 ligase RNF185 expression can be evaluated by any means known to those skilled in the art, including but not limited to assessing the level of the E3 ligase protein of interest using Western blot analysis, for example using an anti-E3 ligase RNF185 antibody, and assessing the level of mRNA for the E3 ligase RNF185 using any available technique, such as quantitative PCR.

According to the invention, an E3 ligase RNF185 inhibitor may be identified as a molecule that reduces the level of activity and/or expression of the E3 ligase RNF185 using any of the methods and assays known in the art and comparing the activity and/or expression of the E3 ligase RNF185 in the presence of the molecule whose E3 ligase RNF185-inhibiting activity is to be assessed with the expression and/or activity of the E3 ligase RNF185 in the absence of any such molecule.

The E3 ligase RNF185 inhibitor of the invention can be of various structural natures and include, without being limited thereto, small molecules, aptamers, antibodies, nucleic acids, lipids, and peptides, polypeptides or proteins able to decrease E3 ligase RNF185 expression and/or activity.

The E3 ligase RNF185 inhibitor may for instance be a peptide or polypeptide, in particular an antibody directed against the E3 ligase RNF185; a nucleic acid molecule which reduces or prevents E3 ligase RNF185 expression, such as an E3 ligase RNF185 anti-sense oligonucleotide; an E3 ligase RNF185 interfering RNA (iRNA) such as siRNA or shRNA; a ribozyme interfering with E3 ligase RNF185 expression; or a small molecule inhibitor of E3 ligase RNF185 activity.

As used herein, the term "small molecule inhibiting the E3 ligase RNF185 activity" refers to a small molecule that can be an organic or inorganic compound, usually less than 1000 daltons, with the ability to inhibit or reduce the activity of the E3 ligase RNF185.

In the context of the invention, the term "aptamer" means a molecule of nucleic acid or a peptide able to bind to an E3 ligase RNF185. The aptamers are nucleic acids, preferably RNA, generally comprising between 5 and 120 nucleotides (Osborne et al., 1997, Curr. Opin. Chem. Biol. 1, 5-9). It refers to a class of molecule that represents an alternative to antibodies in terms of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk, C. and Gold, L., Science, 1990, 249(4968):505-10.

As used in the present invention, the term "antibody" includes to any antibody or antibody-like molecule that has an antigen-binding region, and includes monoclonal antibodies, chimeric antibodies, humanized or human antibodies, recombinant antibodies and fragments or derivatives thereof. Antibody fragment means, for example, F(ab)2, Fab, Fab', single domain antibodies (DABs), or sFv fragments. The techniques for preparing and using various antibody-based constructs and fragments are well-known in the art. Means for preparing and characterizing antibodies are also well-known in the art (see, e.g., Harlow and Lane, 1988).

The inhibition of E3 ligase RNF185 can also be due to the reduction or suppression of the expression of the gene product coding for the E3 ligase RNF185, which ultimately induce a decrease of the protein expression.

In a preferred embodiment of the invention, the E3 ligase RNF185 inhibitor is a nucleic acid comprising or consisting of a sequence capable of hybridizing specifically with a nucleic acid (for example, a gene or an mRNA) coding for an E3 ligase RNF185, and to decrease or suppress the expression of said E3 ligase RNF185.

In the present invention, a "nucleic acid molecule" specifically interfering with E3 ligase gene expression is a nucleic acid molecule which is able to reduce or to suppress the expression of gene coding for said E3 ligase in a specific way. It includes but is not limited to siRNA, antisense and ribozyme molecules. The nucleic acid used according to the invention generally has a length of 10 to 40 nucleotides, preferably from 15 to 30 nucleotides in length.

In the present invention, the nucleic acid is capable of hybridizing specifically to a gene or transcripts coding for an E3 ligase RNF185. By "hybridizing specifically" is intended hybridized in stringent conditions. In particular, stringent conditions can be defined by salt concentration, the concentration of organic solvent (for example, formamide), temperature, and other conditions well-known in the art. Typical stringent hybridization conditions include temperatures above 30° C., preferably above 35° C., more preferably in excess of 42° C., and/or salinity of less than about 500 mM, preferably less than 200 mM. Nevertheless, it is understood that the nucleic acid according to the invention does not need to have 100% complementarity with the target sequence to hybridize specifically. In particular, a nucleic acid with a degree of complementarity at least equal to approximately 90% is capable of hybridizing specifically. Preferably, the degree of complementarity between the nucleic acid according to the invention and the target sequence is equal to at least 95%, 96%, 97%, 98%, 99% or 100%.

The term "complementary" or "complementarity" refers to the ability of polynucleotides to form base pairs with one another. Base pairs are typically formed by hydrogen bonds between nucleotide units in antiparallel polynucleotide strands. Complementary polynucleotide strands can base-pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100 percent complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10 percent complementarity. In the same example, if 18 base pairs on each strand can hydrogen bond with each other, the polynucleotide strands exhibit 90 percent complementarity.

As used herein, the term "siRNA" or "interfering RNA" means any RNA which is capable of down-regulating the expression of the targeted protein. It encompasses small interfering RNA (siRNA), double-stranded RNA (dsRNA), single-stranded RNA (ssRNA), micro-RNA (miRNA), and short hairpin RNA (shRNA) molecules. RNA interference designates a phenomenon by which dsRNA specifically suppresses expression of a target gene at post-translational level. In normal conditions, RNA interference is initiated by double-stranded RNA molecules (dsRNA) of several thousand base pairs in length. In vivo, dsRNA introduced into a cell is cleaved into a mixture of short dsRNA molecules called siRNA. The enzyme that catalyzes the cleavage, Dicer, is an endo-RNase that contains RNase III domains (Bernstein, Caudy et al., Nature, 2001 Jan. 18, 409(6818):

363-6). In mammalian cells, the siRNAs produced by Dicer are 21-23 bp in length, with a 19 or 20 nucleotide duplex sequence, two-nucleotide 3' overhangs and 5'-triphosphate extremities (Zamore, Tuschl et al., Cell, 2000 Mar. 31, 101(1):25-33; Elbashir, Lendeckel et al., Genes Dev., 2001 Jan. 15, 15(2):188-200; Elbashir, Martinez et al., EMBO J., 2001 Dec. 3, 20(23):6877-88).

A number of patents and patent applications have described, in general terms, the use of siRNA molecules to inhibit gene expression, for example, WO 99/32619.

siRNA or shRNA are usually designed against a region 50-100 nucleotides downstream of the translation initiator codon, whereas 5'UTR (untranslated region) and 3'UTR are usually avoided. The chosen siRNA or shRNA target sequence should be subjected to a BLAST search against the EST database to ensure that only the desired gene is targeted. Various products are commercially available to aid in the preparation and use of siRNA or shRNA.

In a preferred embodiment, the RNAi molecule is an siRNA of at least about 10-40 nucleotides in length, preferably about 15-30 base nucleotides.

siRNA or shRNA can comprise naturally-occurring RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end of the molecule or to one or more internal nucleotides of the siRNA, including modifications that make the siRNA resistant to nuclease digestion.

siRNA or shRNA may be administered in free (naked) form or by the use of delivery systems that enhance stability and/or targeting, e.g., liposomes, or incorporated into other vehicles, such as hydrogels, cyclodextrins, biodegradable nanocapsules, bioadhesive microspheres, or proteinaceous vectors, or in combination with a cationic peptide. They may also be administered in the form of their precursors or encoding DNAs. All these techniques are well-known in the art.

In particular, the present invention also contemplates, as an inhibitor, an expression vector encoding an siRNA or an shRNA, preferably an shRNA. Examples of vectors include recombinant viral vectors, in particular an adenoviral, retroviral, adeno-associated viral, lentiviral, herpes simplex viral or Sendai viral vector.

RNF185 inhibitory nucleic acids are commercially available (OriGene, shRNA Ref. TG301946; Qiagen, siRNA Refs. SI03059385, SI03089982, SI04959591, SI04959598).

In a particular embodiment, the nucleic acid molecule specifically interfering with an E3 ligase RNF185 comprises or consists of a sequence selected from the group consisting of:

```
siRNA sequence of SEQ ID No 1:
5'-GAUAUUUGCCACAGCAUUU-3', siRNA sequence of SEQ ID No 2:
5'-CUUCUGUUGGCCGUGUUUA-3' siRNA sequence of SEQ ID No 36:
5'-AGACCAGACCUAACAGACAtt-3'
and siRNA sequence of SEQ ID No 37:
5'-CAUCAGUGGUUGGAGACCAtt-3'
```

Antisense nucleic acid can also be used to down-regulate the expression of the E3 ligase RNF185. The antisense nucleic acid can be complementary to all or part of a sense nucleic acid encoding an E3 ligase RNF185, e.g., complementary to the coding strand of a double-stranded cDNA molecule or complementary to an mRNA sequence, and is thought to interfere with the translation of the target mRNA In a preferred embodiment, the antisense nucleic acid is an RNA molecule complementary to a target mRNA encoding an E3 ligase RNF185.

An antisense nucleic acid can be, for example, about 5, 10, 15, 20, 25, 30, 35, 40, 45 or 50 nucleotides in length. Particularly, antisense RNA molecules are usually 15-50 nucleotides in length. An antisense nucleic acid for use in the invention can be constructed using chemical synthesis and enzymatic ligation reactions using procedures known in the art. Particularly, antisense RNA can be chemically synthesized, produced by in vitro transcription from linear (e.g., PCR products) or circular templates (e.g., viral or non-viral vectors), or produced by in vivo transcription from viral or non-viral vectors. Antisense nucleic acids may be modified to have enhanced stability, nuclease resistance, target specificity and improved pharmacological properties. For example, antisense nucleic acids may include modified nucleotides designed to increase the physical stability of the duplex formed between the antisense and sense nucleic acids.

In the context of the invention, "ribozymes" are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA. Ribozyme molecules specific for functional E3 ligase RNF185 can be designed, produced, and administered by methods commonly known in the art (see, e.g., Fanning and Symonds, 2006, reviewing the therapeutic use of hammerhead ribozymes and small hairpin RNA).

The interfering RNA, the antisense nucleic acids and the ribozyme molecules used according to the invention can be administered in the form of DNA precursors or molecules coding for them.

Preferred RNF185 inhibitors are selected from the group consisting of anti-RNF185 antibody and nucleic acids inhibiting or reducing RNF185 expression, in particular siRNA or shRNA.

In a preferred embodiment, the E3 ligase RNF185 inhibitor is used in combination with an E3 ligase RNF5 inhibitor. The E3 ligase RNF5 inhibitor is preferably selected from the group consisting of a small molecule, an anti-E3 ligase RNF5 antibody, and a nucleic acid inhibiting or decreasing the expression of E3 ligase RNF5, preferably an siRNA or an shRNA. E3 ligase RNF5 inhibitors can be defined as RNF185 inhibitors disclosed in detail above. The person skilled in the art knows how to prepare and/or select an appropriate E3 ligase RNF185 inhibitor. Such inhibitors are also commercially available: antibodies (Pierce Antibodies, ref. PAS-31793; Abcam, refs. ab128200, ab83466, ab135700, and ab154959); siRNA (Qiagen, Refs. SI03157014, SI03221484, SI04204116, SI04251226 and SI05063114); and shRNA (OriGene, Refs. SR304085 and TR318923). Preferred RNF5 inhibitors are selected from the group consisting of anti-RNF5 antibody and nucleic acids inhibiting or reducing RNF5 expression, in particular siRNA or shRNA.

In a particular embodiment, the nucleic acid molecule specifically interfering with an E3 ligase RNF5 comprises or consists of a sequence selected from the group consisting of:

siRNA sequence of SEQ ID No 24:
5'-CCACCGUCUUCAAUGCCCAtt-3' siRNA sequence of SEQ ID No 25:
5'-CGGCAAGAGUGUCCAGUAUtt-3' siRNA sequence of SEQ ID No 26:
5-CUCACUCAGUAACGUUGUUtt-3' (SIGMA)
and siRNA sequence of SEQ ID No 27:
5'-CUGCUCAGAGGCUCACUCAtt-3' (SIGMA).

In a preferred embodiment, the nucleic acid molecule specifically interfering with an E3 ligase RNF5 is an shRNA. More specifically, the shRNA may be prepared with the following 64-base complementary oligonucleotides:

SEQ ID No 28:
5'-GATCCCCAGCTGGGATCAGCAGAGAGttcaagagaCTCTCTGC

TGATCCCAGCTTTTTTGGAAA-3'
and

SEQ ID No 29:
5'-AGCTTTTCCAAAAAAGCTGGGATCAGCAGGAGTCTCTTGAACTC

TCTGCTGATCCCAGCTGGG-3';

SEQ ID No 30:
5'-GATCCCGCGCGACCTTCGAATGTAATTCAAGAGATTACATTCGAA

GGTCGCGCTTTTTTGGAAA-3'
and

SEQ ID No 31:
5'-GCTTTTCCAAAAAAGCGCGACCTTCGAATGTAATCTCTTGAATT

ACATTCGAAGGTCGCGCGG-3' (shRnf5-65);

SEQ ID No 32
5'-GATCCCGAGAAGGTTGTCCCGCTTTATTCAAGAGATAAAGCGGG

ACAACCTTCTTTTTTGGAAA-3'
and

SEQ ID No 33:
5'-AGCTTTTCCAAAAAAGAAGGTTGTCCCGCTTTATCTCTTGAATA

AAGCGGGACAACCTTCTCGG-3' (shRnf5-221);

SEQ ID No 34:
5'-GATCCCGCGCGACCTTCGAATGTAATTTCAAGAGAATTACATTCGA

AGGTCGCGTTTTTTGGAAA-3'
and

SEQ ID No 35:
5'-AGCTTTTCCAAAAAACGCGACCTTCGAATGTAATTCTCTTGAAATT

ACATTCGAAGGTCGCGCGG-3' (shRnf5-66).

The annealed product containing 5' and 3' overhangs compatible with BglII and HindIII restriction sites, respectively was then ligated into pCMS3-cherry digested with BglII and HindIII.

Uses of E3 Ligase RNF185 Inhibitors

The invention then relates to a method for treating cystic fibrosis and/or chronic obstructive pulmonary disease by administering a therapeutically effective amount of an E3 ligase RNF185 inhibitor to patients in need thereof, and to the uses of such E3 ligase RNF185 inhibitor in the treatment of cystic fibrosis and/or chronic obstructive pulmonary disease. It also relates to the use of an E3 ligase RNF185 inhibitor for the manufacture of a medicament for the treatment of cystic fibrosis and/or chronic obstructive pulmonary disease. It relates to an E3 ligase RNF185 inhibitor for use in the treatment of cystic fibrosis and/or chronic obstructive pulmonary disease. Optionally, the E3 ligase RNF185 inhibitor is used in combination with another active ingredient, preferably another compound targeting class II mutation.

Accordingly, the present invention relates to a pharmaceutical composition comprising an E3 ligase RNF185 inhibitor, and optionally a pharmaceutically acceptable carrier, in particular for use in the treatment of cystic fibrosis or chronic obstructive pulmonary disease. The pharmaceutical composition may further comprise another active ingredient, preferably another compound targeting class II mutation.

Advantageously, at least one of the additional compounds targeting class II mutation is an E3 ligase RNF5 inhibitor. Therefore, in a particularly preferred embodiment of the invention, the E3 ligase RNF185 inhibitor is used in combination with an E3 ligase RNF5 inhibitor. Then, in a preferred embodiment, the present invention relates to a pharmaceutical composition comprising an E3 ligase RNF185 inhibitor and an E3 ligase RNF5 inhibitor, and optionally a pharmaceutically acceptable carrier. The invention relates to a method for treating cystic fibrosis and/or chronic obstructive pulmonary disease in a subject in need thereof, comprising administering a pharmaceutically effective amount of a pharmaceutical composition comprising an E3 ligase RNF185 inhibitor and a pharmaceutically effective amount of a pharmaceutical composition comprising an E3 ligase RNF5 inhibitor. Alternatively, the invention relates to a method for treating cystic fibrosis and/or chronic obstructive pulmonary disease in a subject in need thereof, comprising administering a pharmaceutically effective amount of a pharmaceutical composition comprising an E3 ligase RNF185 inhibitor and an E3 ligase RNF5 inhibitor. The present invention also relates to a product comprising (a) an E3 ligase RNF185 inhibitor and (b) an E3 ligase RNF5 inhibitor, as a combined preparation for simultaneous, separate or sequential use as a medicament, and more particularly for use in the treatment of an obstructive pulmonary disease selected from the group consisting of cystic fibrosis and chronic obstructive pulmonary disease. Preferably, the E3 ligase inhibitor is selected from a small molecule, an antibody and a nucleic acid inhibiting or decreasing the expression of E3 ligase. In a preferred embodiment, the E3 ligase RNF185 inhibitor and the E3 ligase RNF5 inhibitor are a combination of siRNA or shRNA. In a preferred and particular embodiment, the RNF185 inhibitor is an shRNA or siRNA and the RNF5 inhibitor is an shRNA. More particularly, the RNF185 inhibitor is an siRNA and the RNF5 inhibitor is an shRNA. In one embodiment, the RNF185 inhibitor is an siRNA of SEQ ID NO: 1 and/or 2, and the RNF5 inhibitor is an shRNA of SEQ ID NO: X.

The terms "kit", "product" or "combined preparation", as used herein, especially define a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is, at different time points, and with equal or different time intervals for any part of the kit of parts. The ratio of the total amounts of the combination partner (a) to the combination partner (b) to be administered in the combined preparation can be varied. The combination partners (a) and (b) can be administered by the same route or by different routes. In a preferred embodiment, partner (b) is administered before or simultaneously with partner (a). When the administration is sequential, the first partner may be, for instance, administered 1, 2, 3, 4, 5, 6, 12, 18 or 24 h before the second partner.

Optionally, it can be further used in combination with an additional active ingredient, in particular another compound targeting class II mutation. More particularly, it can be used in combination with a corrector aimed at restoring CFTR trafficking, a potentiator improving the channel opening and/or a molecule preventing or interfering with the chaperones' recruitment. For instance, a corrector could be another E3 ligase inhibitor.

In the context of the invention, correctors include compounds binding to CFTR molecules and acting on its folding, and therefore named 'pharmacological chaperones', and those acting on the proteostasis network, targeting proteins that regulate CFTR folding and quality control, therefore named proteostasis regulators (PR).

Thus, the pharmaceutical composition of the invention may further comprise a compound already known to affect CFTR expression or stability, such as a pharmacological chaperone or a PR and drugs affecting chaperones. Non-limiting examples of further compounds are 3-(6-(1-(2,2-difluorobenzo[D]-dioxol-5-yl)-cyclopropanecarboxamido)-3-methylpyridin-2-yl)benzoic acid, VRT-325 (4-(cyclohexyloxy)-2-(1-{4-[(4-methoxyphenyl)sulfonyl]-1-piperazinyl}ethyl)quinazoline), VRT-532 (4-methyl-2-(5-phenyl-1H-pyrazol-3-yl)phenol), VX-809 (3-[6-[[1-(2,2-difluoro-1,3-benzodioxol-5-yl)cyclopropanecarbonyl]amino]-3-methylpyridin-2-yl]benzoic acid), C18 (a VX-809 analog), GlyH-101 (CAS Number: 328541-79-3), CFTR Inhibitor 172 (Cas Number: 307510-92-5), DASU-01 (CAS Number: 107410-59-3), Phenylglycine-01 (CAS Number: 853138-65-5), Sulfonamide-03 (SF-03) (CAS Number: 423136-40-7), UCCF-853 (CAS Number: 625458-06-2), dF508act-02 (CAS Number: 298193-32-5), UCCF-029 (CAS Number: 2110-25-0), 3-(3-Butynyl)-5-methoxy-1-phenylpyrazole-4-carbaldehyde (CAS Number: 226070-80-0), UCCF-152 (CAS Number: 601519-76-0), Corr-3a (CAS Number: 362000-44-0), Ataluren (CAS Number: 775304-57-9), Dynasore (CAS Number: 304448-55-3), KM11057 (CAS Number: 708238-13-5), N-(2-Fluorophenyl)-2-(1H-indol-3-yl)-2-oxoacetamide, NS004 (141797-92-4), N-(2-(2-Methoxyphenylamino)-4'-methyl-4,5'-bithiazol-2'-yl) benzamide, Compound 3d (2-(6-Methoxy-4-methyl-quinazolin-2-ylamino)-5,6-dimethyl-pyrimidin-4-ol), Compound 4c (N-[2-(3-Acetyl-phenylamino)-4'-methyl-[4,5']bithiazolyl-2'-yl]-benzamide), N-(2-(2-Methoxyphenylamino)-4'-methyl-4,5'-bithiazol-2'-yl)benzamide, Compound 5c ((4-Bromo-phenyl)-(4-methyl-quinolin-2-yl)-amine), Compound 5a (Phenyl-(4,5,7-trimethyl-quinolin-2-yl)-amine), Corr-2b (Phenyl-[4-(4-vinyl-phenyl)-thiazol-2-yl]-amine), Compound 15JF (CAS Number 958941-60-1), Oxo-172 (CAS number 881816-26-8), 4-(4-Methoxy-3-methylphenyl)-N-(3-methylpyridin-2-yl)thiazol-2-amine, Tetrazolo-172 ((Z)-5-(4-(1H-tetrazol-5-yl)benzylidene)-2-thioxo-3-(3-(trifluoromethyl)phenyl)thiazolidin-4-one), 2-Benzothiazol-2-yl-8-tert-butyl-1,2,4-triaza-spiro[4.5]decane-3-thione, PPQ-102 (CAS Number 931706-15-9), VX-770 (CAS Number: 873054-44-5), benzoic-quinolizinium (MBP) compounds and Corr-4a (CAS Number: 421580-53-2), phosphodiesterases, histone deacetylases, COX-2 inhibitors, poly(ADP)ribose polymerase (PARP), and kinase and Na+/K+ ATPase inhibitors. It may comprise an siRNA or shRNA inhibiting the expression of p97/valosin-containing protein and/or gp78 as taught by WO2007/041282, or of Aha protein as taught by WO2007/137237.

Examples of correctors include, but are not limited to, Corr-3a (CAS Number: 362000-44-0 (6-[(1H-benzimidazol-2-ylthio)methyl]-2-[(6-methoxy-4-methyl-2-quinazolinyl)amino]-4-pyrimidinol)) and VX-809 (3-[6-[[1-(2,2-difluoro-1,3-benzodioxol-5-yl)cyclopropanecarbonyl]amino]-3-methylpyridin-2-yl]benzoic acid), core-corr-II, and corr-4a.

Examples of potentiators include, but are not limited to, VX-770 (CAS Number: 873054-44-5) and VRT-532 (P1).

Examples of molecules preventing or interfering with the chaperones' recruitment include, but are not limited to, Hsp90 inhibitors.

In a particularly preferred embodiment, the present invention relates to the combination of an E3 ligase RNF185 inhibitor, an E3 ligase RNF5 inhibitor and a corrector, in particular VX-809. More specifically, it relates to the combination of E3 ligase RNF185 siRNA or shRNA, E3 ligase RNF5 siRNA or shRNA and VX-809. Such combinations have a synergistic effect. Therefore, such combinations are useful for the treatment of cystic fibrosis or chronic obstructive pulmonary disease.

In a preferred embodiment of the invention, the disease to be treated is cystic fibrosis. More preferably, it is cystic fibrosis with a mutation of class II, namely associated with CFTRΔF508.

As used herein, the term "therapeutically effective amount" is intended an amount of therapeutic agent administered to a patient that is sufficient to constitute a treatment of cystic fibrosis or chronic obstructive pulmonary disease. The amount of an inhibitor of E3 ligase RNF185, and optionally the amount of an inhibitor of E3 ligase RNF5, to be administered has to be determined by standard procedures well-known by those of ordinary skill in the art. Physiological data of the patient (e.g., age, size, and weight), the routes of administration and the disease to be treated have to be taken into account to determine the appropriate dosage.

The inhibitor of E3 ligase RNF185, and optionally the one of E3 ligase RNF5, may be administered as a single dose or in multiple doses. If the inhibitor is a small molecule inhibiting the E3 ligase activity, each unit dosage may contain, for example, from 200 to 1000 mg/kg of body weight, particularly from 500 to 800 mg/kg of body weight. If the inhibitor is an antibody, each unit dosage may contain, for example, from 0.1 to 20 mg/kg of body weight, particularly from 4 to 10 mg/kg of body weight. If the inhibitor is an RNAi, preferably an siRNA or shRNA, each unit dosage may contain, for example, from 2 to 50 mg/kg of body weight, particularly from 5 to 20 mg/kg of body weight.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, Marcel Dekker, New York, 1988-1999) known by a person skilled in the art.

Possible pharmaceutical compositions include those suitable for oral, rectal, intravaginal, mucosal, topical (including transdermal, buccal and sublingual), or parenteral (including subcutaneous, intramuscular, intravenous and intradermal) administration. For these formulations, conventional excipients can be used according to techniques well-known by those skilled in the art.

More particularly, in order to provide a localized therapeutic effect, specific pulmonary administration routes are preferred. In particular, administration by inhalation or insufflation of powders or aerosols, including by nebulizer, is preferred. In a particular embodiment, the E3 ligase inhibitors can be administered after physiotherapy-aided forced expectoration to empty the upper respiratory tract.

Pharmaceutical compositions according to the invention may be formulated to release the active drug substantially immediately upon administration or at any predetermined time or time period after administration.

Screening of E3 Ligase RNF185 Inhibitors

The present invention also concerns a method for identifying or screening molecules useful in the treatment of cystic fibrosis or COPD, preferably cystic fibrosis, based on the ability of such molecules to inhibit the expression and/or activity of an E3 ligase RNF185.

In particular, the invention is drawn to a method for screening comprising the steps of:
a) providing or obtaining a candidate compound; and
b) determining whether said candidate compound inhibits the activity and/or expression of an E3 ligase RNF185,
c) wherein the ability of said candidate compound to inhibit the expression or activity of said E3 ligase RNF185 indicates that said candidate compound is indicative of its usefulness for the treatment of cystic fibrosis.

The candidate compound to be tested in the frame of this method may be of any molecular nature; for example, it may correspond to a chemical molecule (preferably a small molecule), an antibody, a peptide, a polypeptide, an aptamer, an siRNA, a sense or antisense oligonucleotide, or a ribozyme.

The ability of said candidate compound to inhibit the expression or activity of an E3 ligase RNF185 may be tested using any of the methods known to those skilled in the art.

The screening method according to the invention may further comprise, for such candidate compound having the ability to inhibit the expression and/or activity of an E3 ligase RNF185, the step c) of determining whether said candidate compound is able to inhibit the activity or expression of E3 ligase RNF5.

The following examples are given for purposes of illustration and not by way of limitation.

Examples

Material & Method
RNF185 Cloning

Full-length human RNF185 was cloned from HEK293 cells cDNA using Transcriptor High Fidelity cDNA synthesis kit (Roche). It was then PCR-amplified using the following primers: 3' GAAGATCTGCAAGCAAGGGGC-CCTCGGCC 5' (SEQ ID NO: 3) and 3' CCGCTCGAGTTAGGCAATCAGGAGCCAGAACATG 5' (SEQ ID NO: 4) and cloned into BamHI/XhoI sites of pcDNA3.1 Flag expression vector. RNF185 deletion mutants (RNF185 ΔC: 1-176 and RNF185 ΔR: 94-192) were generated by PCR-based cloning of the corresponding fragments using, respectively, the following primers: 3' CCGCTCGAGTTAGCGTGACAGGAACTGCTCGTC 5' (SEQ ID NO: 5) (DOWN) for RNF185 ΔC 3' GAAGATCTAGGGGCAGCACTGGGCAAC 5' (SEQ ID NO: 6) (UP) for RNF185 ΔR. RNF185 RM (C39A, C42A) was generated by PCR-based mutagenesis using the following primers: 3' CGAGGCCAACATCGCCTTGGACACA-GCCAAGGATGCC 5' (SEQ ID NO: 7) (up) and 3' CCAAGGCGATGTTGGCCTCGAAAGTGCTGTCCT-GCC 5' (SEQ ID NO: 8) (down) and cloned along the same strategy used for the WT gene.

The pcDNA3.1 vectors expressing WT CFTR-HA and ΔF508 CFTR-HA, bearing an HA tag epitope in the C-terminal end of the proteins, were a generous gift from M. Benharouga. HA-CD3δ construct was a kind gift from A. Weissman. HA-TCRα was a kind gift from R. Kopito. α-1-antitrypsin-expressing vectors (NHK, Z mutants) were kindly provided by E. Chevet (University of Bordeaux). pEGFP-C1 (Clontech) was used as a control for transfection efficiency. The following antibodies were purchased from commercial vendors: polyclonal anti-α-1-antitrypsin (Dako-Cytomation); monoclonal MM13-4 anti-CFTR (N-terminal tail epitope) (Millipore); monoclonal clone 24-1 anti-CFTR (R&D Systems); polyclonal anti-Derlin-1 antibody (Sigma-Aldrich); monoclonal anti-Erlin-2 (Sigma-Aldrich); monoclonal and polyclonal anti-Flag antibodies (Sigma-Aldrich); monoclonal anti-GAPDH (Ambion); polyclonal anti-GFP (Abcam); monoclonal anti-HA (Covance); and monoclonal anti-ubiquitin (AssayDesign). Polyclonal anti-RNF5 was generated as described in Delaunay et al. ((2008) *PLoS One* 3, e1609/10.1371/journal.pone.0001609). Polyclonal anti-RNF185 was generated by injection of GST-RNF185 recombinant protein into rabbits and affinity purification of the resulting antibodies.

Impact of RNF185 Overexpression on CFTR Protein Levels

HEK293 cells were co-transfected with increasing levels of RNF185 together with a pCDNA3.1 plasmid expressing CFTRΔF508-HA and trace amounts of GFP-expressing plasmid as a control for transfection. The relative levels of CFTR proteins were monitored after immunoblotting and quantified relative to the level of transfection, as defined by the GFP levels.

For immunoblotting experiments, cells were washed with PBS and lysed on ice in buffer A containing 50 mM Tris HCl, pH 8, 150 mM NaCl, 1% Triton 100x, 0.1% SDS, 1 mM EDTA, 0.5% DOC, protease Inhibitor Cocktail Tablets Complete (Roche) and 1 mM PMSF. Equal amounts of proteins were loaded on SDS-PAGE after denaturation (5 minutes at 95° C. or 10 minutes at 42° C. for CFTR samples).

Protein samples were separated on SDS-PAGE (6% acrylamide:bisacrylamide (40% 37.5:1) for CFTR samples or 14% for RNF185 samples) and transferred onto nitrocellulose membranes. After membrane blocking in 5% milk in PBS or in Odyssey blocking buffer (LI-COR Biosciences), immunoblot analysis was performed using the indicated primary antibodies. Anti-mouse IgG or anti-rabbit IgG secondary antibodies labeled with fluorophores of different wavelengths were used to visualize specific protein signals by infrared imaging technology (Odyssey, LI-COR).

RNA Interference Experiments

Small interfering RNAs targeting the 7 isoforms of the human RNF185 gene have been used to transiently inhibit the expression of this ligase in HEK293 cells.

HEK293 cells were transfected at a final concentration of 40 nM with siRNA oligonucleotides directed against RNF185 (5' GAUAUUGCCACAGCAUUU 3' (SEQ ID NO: 1) or 5' CUUCUGUUGGCCGUGUUUA 3' (SEQ ID NO: 2)) or a non-specific control (5' UAGCAAUGAC-GAAUGCGUA 3' (SEQ ID NO: 9)) using the calcium phosphate method. 24 hours later, cells were then transfected with HA-CFTR WT or HA-CFTRΔF508 plasmids. Trace amounts of EGFP-C1 plasmid were co-transfected with CFTR plasmids to control CFTR transfection levels. Cells were then collected 48 hours after the initial siRNA transfection. RNF185 silencing was controlled either by immunoprecipitation using RNF185 antibody followed by immunoblot or by RT-QPCR using RNF185-specific primers.

To perform RNF5/RNF185 double knockdown, stable HEK293 stable cell lines were generated using a control or a validated shRNA sequence targeting RNF5 (WO2008/008874), expressed in pSS-H1 vector (a generous gift from D. Billadeau, Mayo Clinic, Rochester, Minn.) downstream of the RNA polymerase II-dependent H1 promoter. Control or RNF185-directed siRNAs were transfected in stable HEK293 cell lines expressing the control of the RNF5-directed shRNA, together with HA-CFTRΔF508-expressing plasmid. 48 hours after transfection, the stability of the CFTR mutant was monitored over time by monitoring the decrease in CFTR protein levels after addition of the translation inhibitor cycloheximide (100 µg/ml) in the cell culture.

Quantitative PCR Analysis

Cells or tissues were collected and washed in PBS and RNAs were extracted using the Macherey-Nagel RNA extraction kit according to the manufacturer's instructions. 1 µg of RNA was then used for cDNA synthesis using MMLV reverse transcriptase (Invitrogen) and hexaprimers (Roche). Quantitative PCR was then performed using a Bio-Rad iCycler IQ5 PCR Thermal Cycler. The PCR reaction was performed using SYBR Green PCR Master Mix amplification reagent (Invitrogen) and transcript-specific primers. The housekeeping gene GAPDH was used as a reference for cell experiments. 18S RNA and ppia1 genes were used as internal standards for expression analysis in tissues. The transcript-specific primers used are the following: human RNF185 5'-CTGTCACGCCTCTTCCTATTTGT-3' (SEQ ID NO: 45) (forward) and 5'-GCCCAGCATTAG-GCAATCAG-3' (SEQ ID NO: 46) (reverse); mouse RNF185 5'-TCTTCTGTTGGCCGTGTTTACA-3' (SEQ ID NO: 10) (forward) and 5'-TTGCAGACTGGACACACTT-GTC-3' (SEQ ID NO: 11) (reverse); GAPDH: 5'-ATGGGGAAGGTGAAGGTCG-3' (SEQ ID NO: 12) (forward) and 5'-GGGGTCATTGATGGCAACAATA-3' (SEQ ID NO: 13) (reverse); GRP78 5'-CACAGTGGTGC-CTACCAAGA-3' (SEQ ID NO: 14) (forward) and 5'-TGTCTTTTGTCAGGGGTCTTT-3' (SEQ ID NO: 15) (reverse); RN18S 5'-CGCCGCTAGAGGTGAAATTC-3' (SEQ ID NO: 16) (forward) and 5'-TTGGCAAAT-GCTTTCGCTC-3' (SEQ ID NO: 17) (reverse); and PPIA 5'-ATGGCAAATGCTGGACCAAA-3' (SEQ ID NO: 18) (forward) and 5'-GCCTTCTTTCACCTTCCCAAA-3' (SEQ ID NO: 19) (reverse).

For analysis of RNF185 expression upon UPR induction, HEK 293 cells were grown in a six-well plate. 24 hours later, cells were treated with tunicamycin (2 µg/mL) and harvested at the indicated times. The levels of RNF185 and GRP78, used as a control for UPR induction, were evaluated by Q-PCR and quantified using GAPDH as an internal standard.

In Vitro Ubiquitination Assay

Bacterially expressed GST-RNF5, GST-RNF185 and GST-RNF185 RING mutants were purified on FPLC using fast-flow GST columns (GE). In vitro ubiquitination was performed according to the instructions provided with the Ubiquitin Conjugation Initiation Kit (Boston Biochem). Briefly, the assays were carried out at 37° C. in a 30 µl reaction mixture containing 0.5 M HEPES, pH 8.0, 250 nM E1 Enzyme Solution, 600 µM Ubiquitin Solution, 1 mM Mg-ATP Solution, and 0.4 µM of separately provided E2 enzymes. Reactions were terminated by the addition of 20 µL of 5×SDS sample buffer and proteins were separated by 10% SDS-PAGE and visualized by immunoblot using anti-GST and anti-ubiquitin antibodies.

Immunostaining

HEK 293 cells were grown on coverslips and seeded on 24-well plates 24 hours prior to TransIT transfection. The endoplasmic reticulum was visualized by co-transfecting ER-GFP (GFP KDEL) with the indicated plasmids. To visualize the mitochondrial network, cells were treated for 45 min with 100 nM MitoTracker (Invitrogen) in DMSO prior to fixation. Cells were washed in PBS and fixed with 4% formaldehyde in PBS for 30 min. After 3 washes in PBS, cells were permeabilized using 0.5% Triton X100 in PBS. For endogenous RNF185 staining, HEK293 cells were transfected with ER-GFP. 24 hours after transfection cells were washed in PBS and fixed with cold methanol for 4 minutes and processed as described above. Cells were then incubated with 3% BSA in PBS for 30 min. Cells were then incubated with the indicated antibodies (Flag: 1: 50000; GFP: 1: 20000 in BSA 3% PBS). Image acquisition was done on a Zeiss LSM510 Meta confocal microscope (Plan-Apochromat 63×1.4-numerical-aperture [NA1.4] objective). Images were further analyzed using ImageJ and Adobe Photoshop CS6 software.

Analysis of E2 Ligase Function

Ubc6 function was blocked by using dominant negative versions of UBE2J1 (Ubc6e) and UBE2J2. UBE2J1 and UBE2J2 plasmids were kind gifts from Hidde Ploegh and Alan Weissman, respectively. UbcH5 function was assessed by simultaneous knockdown of UbcH5a, UbcH5b and UbcH5c using siRNA pool as follows: a pool of 5'-CCAAAGAUUGCUUUCACAAUU-3' (SEQ ID NO: 20) and 5'-GGUGGAGUCUUCUUUCUCAUU-3' (SEQ ID NO: 21) targeting UbcH5a, 5'-CAGUAAUGGCAG-CAUUUGU-3' (SEQ ID NO: 22) targeting UbcH5b and 5'-GAUCACAGUGGUCGCCUGC-3' (SEQ ID NO: 23) targeting UbcH5c. UbcH5 knockdown efficiency was controlled by using UbcH5 antibody (Boston Biochem).

Analysis of CHIP Function

CHIP function was assessed by knockdown of CHIP using siRNA pool as follows: a pool of 5' CAGACUUU-GUCAUGGAGCU dTdT (SEQ ID NO: 43) and 5' GUCAU-GUGGUGCCUCUGGU dTdT (SEQ ID NO: 44). SiRNAs were used at 40 nM as previously disclosed.

Vx-809

VX-809 was used at a concentration of 5 µM in DMSO (Van Goor et al., PNAS, 2011).

Results

RNF185 is a Conserved Ubiquitous E3 Ligase of Higher Eukaryotes

Figure 2:
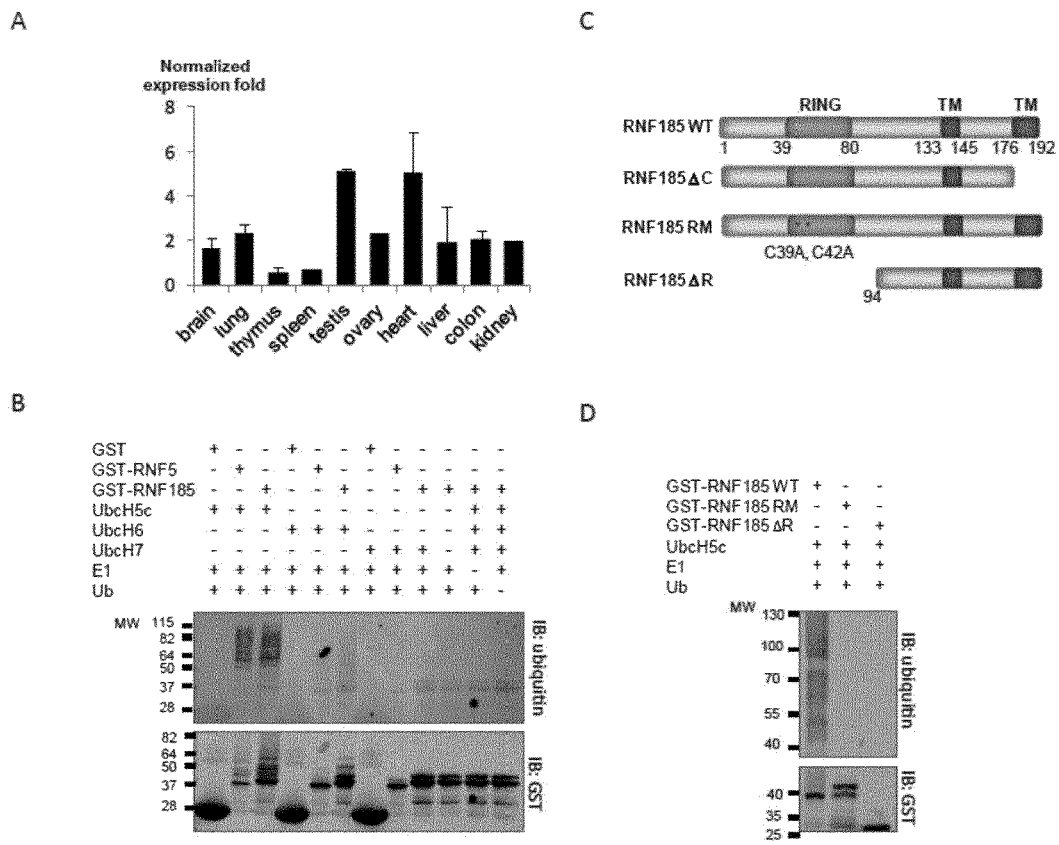
FIG. 2. RNF185 is a novel ubiquitously expressed E3 ligase.

By performing a BLAST analysis against the human RNF5 protein, the inventors identified human RNF185, which exhibits more than 70% of sequence identity with RNF5. Apart from the RING domain, a high degree of sequence identity is found both in the two C-terminal transmembrane domains and in the central region (FIG. 1). By searching sequence databases, the inventors identified homologs of RNF5 and RNF185 in several species. Interestingly, only one family member was found in nematodes and no members could be found in S. cerevisiae, although RNF5/RNF185 homologs exist in specific fungi and in amoebae. As shown by quantitative-PCR, RNF185 is widely expressed in mouse tissues with high levels of expression in the heart and testis (FIG. 2A).

To test the activity of RNF185 as a bona fide RING-dependent E3 ligase, the inventors performed in vitro self-ubiquitination assays with GST-purified recombinant RNF185, in the presence of ubiquitin, ATP, E1 and different E2 enzymes. Auto-ubiquitination was monitored by Western blot using an anti-ubiquitin antibody (FIG. 2B). In the presence of UbcH5c, GST-RNF185 exhibited a potent self-ubiquitination activity that was comparable to that observed for RNF5. Self-ubiquitination, although much lower, could also be detected in the presence of UbcH6, but was absent in the presence of UbcH7. The inventors next tested the requirement of the RING domain for the ubiquitination activity of RNF185 by introducing two point mutations at cysteine 39 and 42 (RNF185 RM) or by truncating the entire RING domain (RNF185 ΔR) (see FIG. 2C). These mutants were both devoid of auto-ubiquitination activity (FIG. 2D), establishing that RNF185 has a RING-dependent E3 ligase activity.

RNF185 Localizes to the ER Membrane and Interacts with ERAD Components

Fluorescence microscopy was used to localize an N-terminal Flag-tagged version of RNF185. In the HEK293, HeLa and RPE cell lines, RNF185 largely co-localized with the GFP-KDEL ER marker. Further, in HEK293, endogenous RNF185 also localized to the ER, as shown using an antibody raised against RNF185. A previous report indicated that RNF185 localizes to mitochondria and not to the ER (Tang et al. (2011) Plos One; 6(9):e24367. doi: 10.1371), in discordance with their observations. The inventors therefore compared the imaging-fluorescence signal of Flag-tagged RNF185 with that of Mitotracker. Although the inventors could not totally discount a mitochondrial localization, the ER localization of RNF185 appeared clearly predominant in their experimental conditions.

The inventors next inspected the localization of Flag-tagged mutants of RNF185 in HEK293 cells. RNF185 ΔC, a mutant with a truncation of the most distal transmembrane domain (amino acids 176 to 192), did not localize to the ER, but instead displayed a diffuse fluorescence pattern, indicating that this domain is required for ER membrane targeting. In contrast, both RING mutants RNF185 RM and RNF185 ΔR essentially localized to the ER structure, indicating that the E3 ligase activity of RNF185 is not required for its localization.

Having shown that RNF185 is an E3 ligase localized in the ER, the inventors next probed the interaction of its Flag-tagged version with select ERAD components by Flag-immunoprecipitation in HEK293T cells. Flag-RNF185 could efficiently pull down Derlin-1, as reported for Flag-RNF5 (FIG. 4A). Flag-RNF185, as well as Flag-RNF5, also efficiently pulled down Erlin-2 (FIG. 4A), a prohibitin-like scaffold protein of the ERAD that has been reported to target IP3R (Pearce, M. M., et al., J. Biol. Chem. 282, 20104-20115/10.1074/jbc.M701862200). The inventors next probed the RNF185 interaction with Ubc6 and Ubc7, which are the two ER membrane-associated E2 ligases of ERAD. Flag-RNF185 efficiently pulled down both Ubc6e/UBE2J1 and UBE2J2 (FIG. 4B), but not Ubc7/UBE2G1 (data not shown), indicating a preferential association of RNF185 with the Ubc6 E2 ligase family.

As ERAD components are transcriptionally induced as part of the UPR (Christianson et al. (2012) Nat. Cell. Biol. 14, 93-105; Travers, K. J. et al. (2000) Cell 101, 249-258/10847680), the inventors monitored RNF185 expression upon treatment with tunicamycin, a drug causing ER stress by blocking glycosylation. RNF185 transcripts increased in response to tunicamycin, peaking at 12 hours after the onset of treatment (FIG. 4C, left panel), a time-course comparable to that observed for the bona fide UPR target GRP78 (FIG. 4C, right panel).

In summary, the inventors conclude that RNF185 is a RING domain-dependent E3 ligase of the ER that interacts with ERAD components and is transcriptionally induced during the UPR.

RNF185 Targets CFTR and CFTRΔF508 to ERAD

The data strongly suggest a role of RNF185 in ERAD. To further substantiate this hypothesis, the inventors checked whether modulating RNF185 cellular levels would affect the stability of ERAD model substrates. CFTR and CFTRΔF508 are both targeted to ERAD, due to inefficient folding, which leads to the degradation of two-thirds of the former and 99% of the latter. CFTR migrates as two bands; the faster one represents the immature ER-localized B form, and the slower one the plasma membrane-localized mature C form (FIG. 5A, upper panels). CFTRΔF508 is only seen as the ER-retained immature B form. In cells overexpressing RNF185, the levels of both CFTR and CFTRΔF508 dramatically decreased, in proportion with the dose of RNF185 (FIG. 5A). Such an effect was dependent on RNF185 ubiquitin ligase activity, as it was not seen with the RING mutants RNF185 RM or RNF185 ΔR (FIG. 5B). At the highest dose of RNF185, intensity of the wild-type CFTR C form band was 5-fold lower (FIG. 5A, lane 4, 2 μg of DNA) than that of the control sample (FIG. 5A, lane 1). The RNF185-dependent decrease of the wild-type CFTR C form reflects an increased degradation of the ER-localized B form rather than a block in maturation, as suggested by the concerted change of immature and mature CFTR.

CFTRΔF508 levels also showed a 5-fold decrease upon RNF185 expression. Such a decrease was already seen at the lowest dose of RNF185 (FIG. 5A), which suggests that CFTRΔF508 is more sensitive to RNF185-dependent degradation than CFTR.

The inventors next evaluated the impact of RNF185 knockdown on the levels of CFTR proteins, using an RNF185-specific siRNA that potently extinguished RNF185 expression up to 80% (FIG. 5C and FIG. 3). Under this condition, the intensity of the CFTR C form increased by 2-fold (202%). A minor increase of the intensity of the CFTR B form (121%) was also observed, again indicating that RNF185 affects CFTR turnover and not maturation (FIG. 5C). Knockdown of RNF185 also resulted in a 2-fold increase in the intensity of the CFTRΔF508 B form, but did not promote the appearance of the C form. The effect of the RNF185 knockdown was also observed in a cell line stably expressing CFTRΔF508 (FIG. 3).

As a further indication of RNF185 and CFTR's functional relationship, the inventors checked their interaction by co-immunoprecipitation. Immunoprecipitation of either HA-CFTR or HA-CFTRΔF508 could efficiently pull down RNF185 or RNF185 RM in cells co-expressing these proteins, but not in cells that did not (FIG. 5D, upper panel). Conversely, RNF185 RM immunoprecipitated HA-CFTRΔF508 and the B form but not the C form of HA-CFTR (FIG. 5D, lower panel), validating their functional interaction in the ER. Association with wild-type RNF185 was tested in the presence of the proteasome inhibitor MG132 to prevent RNF185-induced CFTR degradation (see below).

The inventors also checked whether, in addition to CFTR, RNF185 could target other ERAD model substrates. TCRα and CD3δ are type I transmembrane proteins recognized as abnormal T-cell receptor subunits when individually expressed and, as such, are degraded by ERAD. The NHK and Z variants are folding-defective mutants of the ER luminal enzyme a1-antitrypsin (AAT). While the NHK mutant is a bona fide ERAD substrate, the Z variant is cleared up by both the proteasomal and autophagic pathways. Overexpressing RNF185 did not affect the stability of any of these proteins. Overexpressing E3 ligase RING mutants can cause dominant negative effects by titration of their substrates away from E2-dependant ubiquitination. However, neither of the RNF185 RING mutants had an effect on the stability of the isolated TCR α or mutant AATs.

Overall, these data indicate that RNF185 is a novel ER E3 ligase that regulates CFTR turnover.

RNF185 Affects CFTR and CFTRΔF508 Stability Through the Ubiquitin-Proteasome System.

To evaluate whether RNF185 affects CFTR turnover through proteasomal degradation, the inventors monitored the effect of the proteasome inhibitor ALLN (N-Acetyl-L-leucinyl-L-leucinyl-L-Norleucinal-CHO). Consistent with previous observations by Ward et al. (Cell, 1995, 83, 121-127), proteasome inhibition strongly stabilized WT and mutant CFTR, with preferential accumulation of the immature B form in both the detergent-soluble and detergent-insoluble fractions (FIG. 5E). ALLN also mitigated the RNF185-dependent decrease of both CFTR and CFTRΔF508 levels, an effect that was more pronounced for the latter. To detect CFTR-ubiquitin conjugates, the inventors blocked protein deubiquitination by adding N-ethylmaleimide during the lysis of cells that were otherwise treated with proteasome inhibitors (FIG. 9). In both ALLN and MG132-treated cells, the amount of CFTR ubiquitin conjugates increased in the presence of RNF185, which indicates that RNF185 targets CFTR to ubiquitin-proteasome-dependent degradation.

As shown in FIG. 4B, RNF185 interacts with the E2 ligases Ubc6e/UBE2J1 and UBE2J2, the former of which is known to regulate CFTR turnover. The inventors thus evaluated the role of these E2 ligases in RNF185-dependent CFTR degradation. Co-expressing RNF185 and Ubc6e/UBE2J1 had an additive effect on CFTRΔF508 levels' decrease that was not seen with the catalytically dead Ubc6eC91S (FIG. 9; compare lane 2 and 3 with lane 4). These data suggest that these two enzymes cooperate in CFTR degradation. However, the inventors could not observe a rescue of the RNF185-dependent degradation of CFTRΔF508 following Ubc6eC91S overexpression, an effect that would be expected on the basis of a transdominant negative effect of Ubc6eC91S. Therefore, either Ubc6eC91S does not behave as a transdominant negative mutant in these conditions, or alternatively another E2 ligase cooperates with RNF185 to degrade CFTR. RNF185 also interacted with UBE2J2 (see FIG. 4B), yet simultaneously co-expressing both Ubc6 dominant-negative mutants did not prevent RNF185-dependent degradation of CFTR (data not shown). UbcH5 is also known to regulate CFTR degradation and knocking down expression of all three UbcH5 isotypes (a, b and c) rescued RNF185-dependent CFTR levels' decrease, but only partially. This suggests that the UbcH5 family could also serve as E2 ligases for RNF185.

RNF185 Affects CFTR Co-Translational Degradation

The inventors next sought to quantify the change in the rate of CFTRΔF508 degradation prompted by RNF185 over-expression through a measure of CFTRΔF508 half-life, after inhibiting translation with cycloheximide (CHX) (FIG. 6). Upon RNF185 overexpression, the increased degradation of CFTRΔF508 was reflected by a decrease of its half-life from 44 minutes to 29 minutes in the presence of RNF185 (FIG. 6A). Upon RNF185 knockdown however, despite an elevated level of CFTRΔF508 at the initial time point, the CFTRΔF508 half-life was not significantly altered (FIG. 6B). The CHX-based protocol only reports on the stability of fully translated CFTR protein, ignoring any co-translational degradation. To evaluate whether RNF185 could preferentially affect CFTRΔF508 stability during translation, the inventors monitored the accumulation of metabolically labeled CFTRΔF508 after adding $^{35}$S-Met/$^{35}$S-Cys for a defined period of time (FIG. 7A). As expected, the amount of labeled CFTRΔF508 increased with time, but the over-expression of RNF185 decreased CFTRΔF508 labeling by up to 50% compared to the control condition and this, at all time points examined. The pulse-labeling experiment measures the net balance between protein translation and degradation, the latter occurring after and possibly also during translation. To exclude an impact of RNF185 on CFTR translation efficiency, the inventors repeated the pulse-labeling experiment in the presence of the proteasome inhibitor ALLN. ALLN totally corrected the RNF185-dependent decrease of the amount of $^{35}$S-labeled protein at all the time points tested (FIG. 7A), which indicates that RNF185 over-expression only affects CFTR degradation and not translation. The rate of post-translational degradation can be calculated from a fitted curve deduced from the values obtained in the CHX experiment, and this rate can then be used to predict the impact of post-translational degradation on the amount of accumulated $^{35}$S-labeled CFTRΔF508. Such calculation predicts that the decrease in the amount of $^{35}$S-labeled CFTR caused by RNF185 over-expression at 20 min would be 7% at best, if degradation was exclusively post-translational, a decrease much lower than the 35-50% decrease observed in the pulse experiment (FIG. 7B). The inventors thus conclude that upon overexpression, RNF185 targets CFTR proteins for ubiquitination and degradation both during and after protein synthesis.

The inventors next performed the same experiment in conditions upon RNF185 knockdown (FIG. 7C). Strikingly, the amount of accumulated $^{35}$S-labeled CFTRΔF508 was at least twice the control condition. As RNF185 knockdown did not affect the rate of CFTR post-translational turnover (see FIG. 6B), these data again point to a preferential effect of RNF185 on CFTR stability during synthesis.

RNF5 and RNF185 have a Redundant Function on the Control of CFTR Stability

The control of CFTR co-translational degradation has previously been attributed to RNF5. The inventors therefore compared the impact of RNF5 and RNF185 knockdown on CFTR turnover. HEK293 cells stably expressing an RNF5-directed shRNA sequence succeeded, as it caused a 3-fold increase in CFTRΔF508 steady-state levels (FIG. 8), compared to the 2-fold increase observed upon RNF185 knockdown (see FIG. 5C, FIG. 8). As already shown above for RNF185, the effect of each single knockdown mainly reflected an E3 ligase-dependent co-translational regulation of CFTR stability, as each did not significantly impact CFTRΔF508 turnover rate after CHX addition (FIG. 6 and FIG. 8). The inventors next monitored the impact of knocking down RNF5 and RNF185 simultaneously. Strikingly, the combined depletion of both ligases led to a drastic stabilization of CFTRΔF508. This was reflected by a 4.5-fold increase in CFTRΔF508 steady-state levels, and also by a net decrease of CFTR turnover rates after CHX addition. Importantly, the pool of stabilized CFTRΔF508 was only found in the Triton soluble fraction, indicating that stabilized CFTR proteins do not form aggregates and should be accumulating in a foldable state.

These data strongly suggest that RNF5 and RNF185 are functionally redundant in the control of CFTR stability. Moreover, they reveal a new overlapping function for these enzymes in the post-translational control of CFTR stability.

CONCLUSION

Figure 8B:
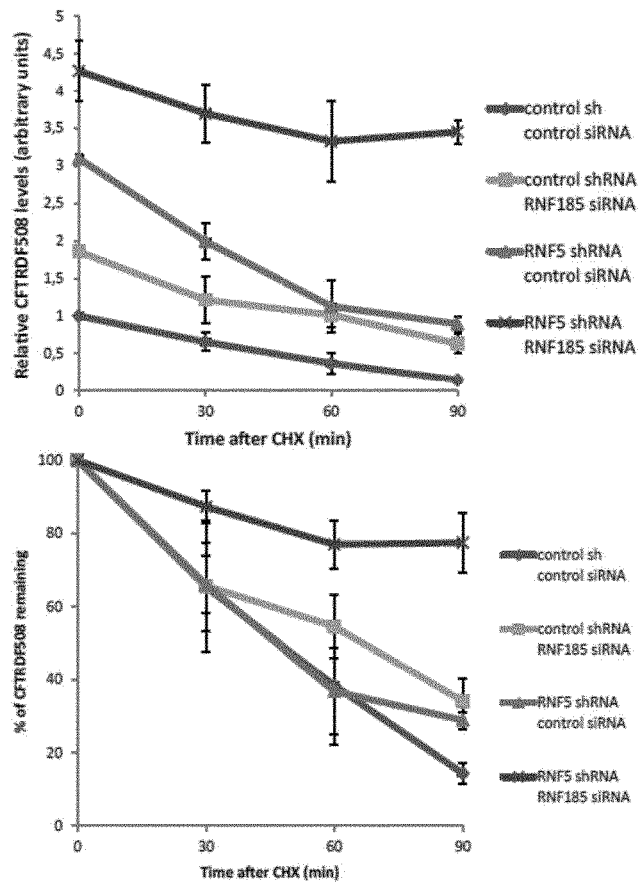

The inventors have identified RNF185 as a new E3 ligase that drives CFTR degradation in the ER, a function that appears redundant with RNF5. These data expand the repertoire of mammalian E3 ligases that operate in ERAD. Importantly, they provide key information for setting up strategies to efficiently block CFTR degradation in the ER and to increase the pool of foldable CFTR, potentially operational for maturation and plasma membrane targeting. Importantly, the inventors have shown that, as RNF5, RNF185 can target mutant CFTRΔF508 to co-translational degradation, i.e., while the CFTR protein is being synthesized (FIGS. 6 and 7). The inventors provided new data showing that simultaneously inhibiting RNF185 and RNF5 results in a profound stabilization of CFTRΔF508 (FIG. 8), greater than that obtained following single depletion of RNF5 or RNF185. Importantly, the data indicate that such stabilization is not only due to the known function of RNF5 (Younger et al., 2006) and function of RNF185 (FIGS. 6 and 7) in CFTR co-translational quality control but also to their redundant function in regulating CFTR post-translational turnover rates (FIG. 8). Indeed, the invention confirms (FIG. 8) that single depletion of each ligase does increase CFTR steady-state levels but does not affect CFTR post-translational turnover rates measured after translation has been blocked by cycloheximide (CHX) treatment. Furthermore, the invention shows that the combined knockdown of RNF5 and RNF185 affects not only CFTR-steady state levels but also its post-synthetic turnover rates (compare FIG. 8B left and right panels) measured after CHX. Such effect could only be uncovered once both E3 ligases RNF5 and RNF185 have been depleted and was unexpected as RNF5 was previously proposed to act only co-translationally (Younger et al., 2006). Similarly, RNF185 single knockdown experiments pointed to its preferred role during CFTR translation (FIGS. 6 and 7). This should be explained by the ability of one ligase to compensate for the loss of the other, suggesting that mechanistically, RNF5 and RNF185 may sense similar CFTR folding defects on the full-length protein. In other words RNF5 and RNF185 appear fully redundant after the synthesis of the full-length CFTR and the invention uncovers for the first time their function in regulating the fate of full-length CFTR in the ER that could not be seen upon inactivation of either E3 ligase.

Knockdown of RNF5 and RNF185 Synergizes with Vx-809 Treatment to Restore CFTR Maturation Data as shown in FIG. 10 indicate that stabilization of F508del-CFTR leads to the accumulation of CFTR proteins, amenable to correction by the chemical chaperone Vx-809. These data therefore suggest that RNF5/RNF185 inhibition would act synergistically together with pharmacological chaperones to restore CFTR function.

CHIP Knockdown does not Further Stabilize F508del-CFTR in RNF5/RNF185 Double Knockdown Cells As shown in FIG. 11, CHIP downregulation does not enhance CFTR stability alone or in the absence of RNF5 and RNF185, ruling out a major role of CHIP in CFTR ERAD. These data thus indicate that RNF5/RNF185 constitutes the major module controlling CFTR ER degradation.

The invention claimed is:

1. A method of treating cystic fibrosis or chronic obstructive pulmonary disease (COPD) comprising administering a composition comprising an E3 ligase RNF185 (Ring Finger Protein) inhibitor and an E3 ligase RNF5 inhibitor to a patient having cystic fibrosis or chronic obstructive pulmonary disease, wherein the E3 ligase RNF185 inhibitor is selected from the group consisting of an interfering RNA, a siRNA and a shRNA that inhibits or decreases the expression of E3 ligase RNF185, and wherein the E3 ligase RNF5 inhibitor is selected from the group consisting of an interfering RNA, a siRNA and a shRNA that inhibits or decreases the expression of E3 ligase RNF5.

2. The method according to claim 1, wherein the E3 ligase RNF185 inhibitor and the E3 ligase RNF5 inhibitor are a combination of siRNA or shRNA.

3. The method according to claim 1, wherein the patient being treated has cystic fibrosis associated with CFTRΔF508.

4. A pharmaceutical composition comprising an E3 ligase RNF185 inhibitor and an E3 ligase RNF5 inhibitor, wherein the E3 ligase RNF185 inhibitor is selected from the group consisting of an interfering RNA, a siRNA and a shRNA that inhibits or decreases expression of E3 ligase RNF185, and wherein the E3 ligase RNF5 inhibitor is selected from the group consisting of an interfering RNA, an siRNA and an shRNA that inhibits or decreases the expression of E3 ligase RNF5.

5. The pharmaceutical composition according to claim 4, further comprising a CFTR corrector that restores CFTR trafficking.

6. The pharmaceutical composition according to claim 4, wherein said composition comprises:

a) an E3 ligase RNF185 inhibitor selected from a siRNA comprising:

```
SEQ ID NO: 1:  5'-GAUAUUUGCCACAGCAUUU-3',
SEQ ID NO: 2:  5'-CUUCUGUUGGCCGUGUUUA-3'
SEQ ID NO: 36: 5'-AGACCAGACCUAACAGACAtt-3'
and
SEQ ID NO: 37: 5'-CAUCAGUGGUUGGAGACCAtt-3';
``` b) an E3 ligase RNF5 inhibitor selected from a shRNA comprising:

```
SEQ ID NO: 28: 5'-GATCCCCAGCTGGGATCAGCAGAGAGttcaag
agaCTCTCTGCTGATCCCAGCTTTTTTGGAAA-3'
and SEQ ID NO: 29: 5'-AGCTTTTCCAAAAAAGCTGGGATCAGCAGGAG
TCTCTTGAACTCTCTGCTGATCCCAGCTGGG-3';

SEQ ID NO: 30: 5'-GATCCCGCGCGACCTTCGAATGTAATTCAAG
AGATTACATTCGAAGGTCGCGCTTTTTTGGAAA-3'
and SEQ ID NO: 31: 5'-GCTTTTCCAAAAAAGCGCGACCTTCGAATGT
AATCTCTTGAATTACATTCGAAGGTCGCGCGG-3' (shRnf5-65);

SEQ ID NO: 32: 5'-GATCCCGAGAAGGTTGTCCCGCTTTATTCA
AGAGATAAAGCGGGACAACCTTCTTTTTTGGAAA-3'
and SEQ ID NO: 33: 5'-AGCTTTTCCAAAAAAGAAGGTTGTCCCGCTT
TATCTCTTGAATAAAGCGGGACAACCTTCTCGG-3' (shRnf5-221);

SEQ ID NO: 34: 5'-GATCCCGCGCGACCTTCGAATGTAATTTCAA
GAGAATTACATTCGAAGGTCGCGTTTTTTGGAAA-3'
and SEQ ID NO: 35: 5'-AGCTTTTCCAAAAAACGCGACCTTCGAATGT
AATTCTCTTGAAATTACATTCGAAGGTCGCGCGG-3' (shRnf5-66);
``` and c) a corrector that restores CFTR trafficking selected from: Corr-3a (CAS Number: 362000-44-0 (6-[(1H-benzimidazol-2-ylthio)methyl]-2-[(6-methoxy-4-methyl-2-quinazolinyl)amino]-4-pyrimidinol)) and VX-809 (3-[6-[[1-(2,2-difluoro-1,3-benzodioxol-5-yl)cyclopropanecarbonyl]amino]-3-methylpyridin-2-yl]benzoic acid).

7. The pharmaceutical composition according to claim 6, wherein said composition comprises SEQ ID NO: 1, an shRNA comprising SEQ ID NOs: 28 and 29 and VX-809.

* * * * *

UNITED STATES PATENT AND TRADEMARK OFFICE
CERTIFICATE OF CORRECTION

PATENT NO. : 10,047,362 B2
APPLICATION NO. : 14/910941
DATED : August 14, 2018
INVENTOR(S) : Agnès Delaunay-Moisan and Michel Toledano Page 1 of 1

It is certified that error appears in the above-identified patent and that said Letters Patent is hereby corrected as shown below:

In the Specification

Column 9,
Line 14, "RINGS" should read --RING5--.

Column 14,
Line 57, "ref. PAS-31793" should read --ref. PA5-31793--.

Column 20,
Line 17, "(Abeam)" should read --(Abcam)--.

Column 24,
Line 62, "enzyme al-antitrypsin" should read --enzyme α1-antitrypsin--.

Signed and Sealed this
Twentieth Day of August, 2019

Andrei Iancu
*Director of the United States Patent and Trademark Office*

SEQUENCE LISTING

```
<160> NUMBER OF SEQ ID NOS: 45

<210> SEQ ID NO 1
<211> LENGTH: 19
<212> TYPE: DNA
<213> ORGANISM: artificial sequence
<220> FEATURE:
<223> OTHER INFORMATION: siRNA

<400> SEQUENCE: 1
gauauuugcc acagcauuu                                                    19

<210> SEQ ID NO 2
<211> LENGTH: 19
<212> TYPE: DNA
<213> ORGANISM: artificial sequence
<220> FEATURE:
<223> OTHER INFORMATION: siRNA

<400> SEQUENCE: 2
cuucuguugg ccuguuua                                                     19

<210> SEQ ID NO 3
<211> LENGTH: 29
<212> TYPE: DNA
<213> ORGANISM: artificial sequence
<220> FEATURE:
<223> OTHER INFORMATION: primer

<400> SEQUENCE: 3
gaagatctgc aagcaagggg ccctcggcc                                         29

<210> SEQ ID NO 4
<211> LENGTH: 34
<212> TYPE: DNA
<213> ORGANISM: artificial sequence
```

```
<220> FEATURE:
<223> OTHER INFORMATION: primer

<400> SEQUENCE: 4
ccgctcgagt taggcaatca ggagccagaa catg                                34

<210> SEQ ID NO 5
<211> LENGTH: 33
<212> TYPE: DNA
<213> ORGANISM: artificial sequence
<220> FEATURE:
<223> OTHER INFORMATION: primer

<400> SEQUENCE: 5
ccgctcgagt tagcgtgaca ggaactgctc gtc                                 33

<210> SEQ ID NO 6
<211> LENGTH: 27
<212> TYPE: DNA
<213> ORGANISM: artificial sequence
<220> FEATURE:
<223> OTHER INFORMATION: primer

<400> SEQUENCE: 6
gaagatctag gggcagcact gggcaac                                        27

<210> SEQ ID NO 7
<211> LENGTH: 37
<212> TYPE: DNA
<213> ORGANISM: artificial sequence
<220> FEATURE:
<223> OTHER INFORMATION: primer

<400> SEQUENCE: 7
cgaggccaac atcgccttgg acacagccaa ggatgcc                             37

<210> SEQ ID NO 8
<211> LENGTH: 36
<212> TYPE: DNA
<213> ORGANISM: artificial sequence
<220> FEATURE:
<223> OTHER INFORMATION: primer

<400> SEQUENCE: 8
ccaaggcgat gttggcctcg aaagtgctgt cctgcc                              36

<210> SEQ ID NO 9
<211> LENGTH: 19
<212> TYPE: DNA
<213> ORGANISM: artificial sequence
<220> FEATURE:
<223> OTHER INFORMATION: primer

<400> SEQUENCE: 9
uagcaaugac gaaugcgua                                                 19

<210> SEQ ID NO 10
<211> LENGTH: 22
<212> TYPE: DNA
<213> ORGANISM: artificial sequence
<220> FEATURE:
<223> OTHER INFORMATION: primer

<400> SEQUENCE: 10
tcttctgttg gccgtgttta ca                                             22
```

```
<210> SEQ ID NO 11
<211> LENGTH: 22
<212> TYPE: DNA
<213> ORGANISM: artificial sequence
<220> FEATURE:
<223> OTHER INFORMATION: primer

<400> SEQUENCE: 11
ttgcagactg gacacacttg tc                                              22

<210> SEQ ID NO 12
<211> LENGTH: 19
<212> TYPE: DNA
<213> ORGANISM: artificial sequence
<220> FEATURE:
<223> OTHER INFORMATION: primer

<400> SEQUENCE: 12
atggggaagg tgaaggtcg                                                  19

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
ggggtcattg atggcaacaa ta                                              22

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
cacagtggtg cctaccaaga                                                 20

<210> SEQ ID NO 15
<211> LENGTH: 21
<212> TYPE: DNA
<213> ORGANISM: artificial sequence
<220> FEATURE:
<223> OTHER INFORMATION: primer

<400> SEQUENCE: 15
tgtcttttgt cagggtctt t                                                21

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
cgccgctaga ggtgaaattc                                                 20

<210> SEQ ID NO 17
<211> LENGTH: 19
<212> TYPE: DNA
<213> ORGANISM: artificial sequence
<220> FEATURE:
<223> OTHER INFORMATION: primer
```

-continued

```
<400> SEQUENCE: 17
ttggcaaatg ctttcgctc                                                  19

<210> SEQ ID NO 18
<211> LENGTH: 20
<212> TYPE: DNA
<213> ORGANISM: artificial sequence
<220> FEATURE:
<223> OTHER INFORMATION: primer

<400> SEQUENCE: 18
atggcaaatg ctggaccaaa                                                 20

<210> SEQ ID NO 19
<211> LENGTH: 21
<212> TYPE: DNA
<213> ORGANISM: artificial sequence
<220> FEATURE:
<223> OTHER INFORMATION: primer

<400> SEQUENCE: 19
gccttctttc accttcccaa a                                               21

<210> SEQ ID NO 20
<211> LENGTH: 21
<212> TYPE: DNA
<213> ORGANISM: artificial sequence
<220> FEATURE:
<223> OTHER INFORMATION: siRNA

<400> SEQUENCE: 20
ccaaagauug cuuucacaau u                                               21

<210> SEQ ID NO 21
<211> LENGTH: 21
<212> TYPE: DNA
<213> ORGANISM: artificial sequence
<220> FEATURE:
<223> OTHER INFORMATION: siRNA

<400> SEQUENCE: 21
gguggagucu ucuuucucau u                                               21

<210> SEQ ID NO 22
<211> LENGTH: 19
<212> TYPE: DNA
<213> ORGANISM: artificial sequence
<220> FEATURE:
<223> OTHER INFORMATION: siRNA

<400> SEQUENCE: 22
caguaauggc agcauuugu                                                  19

<210> SEQ ID NO 23
<211> LENGTH: 19
<212> TYPE: DNA
<213> ORGANISM: artificial sequence
<220> FEATURE:
<223> OTHER INFORMATION: siRNA

<400> SEQUENCE: 23
gaucacagug gucgccugc                                                  19

<210> SEQ ID NO 24
```

```
<211> LENGTH: 21
<212> TYPE: DNA
<213> ORGANISM: artificial sequence
<220> FEATURE:
<223> OTHER INFORMATION: siRNA

<400> SEQUENCE: 24
ccaccgucuu caaugcccat t                                                   21

<210> SEQ ID NO 25
<211> LENGTH: 21
<212> TYPE: DNA
<213> ORGANISM: artificial sequence
<220> FEATURE:
<223> OTHER INFORMATION: siRNA

<400> SEQUENCE: 25
cggcaagagu guccaguaut t                                                   21

<210> SEQ ID NO 26
<211> LENGTH: 21
<212> TYPE: DNA
<213> ORGANISM: artificial sequence
<220> FEATURE:
<223> OTHER INFORMATION: siRNA

<400> SEQUENCE: 26
cucacucagu aacguuguut t                                                   21

<210> SEQ ID NO 27
<211> LENGTH: 21
<212> TYPE: DNA
<213> ORGANISM: artificial sequence
<220> FEATURE:
<223> OTHER INFORMATION: siRNA

<400> SEQUENCE: 27
cugcucagag gcucacucat t                                                   21

<210> SEQ ID NO 28
<211> LENGTH: 64
<212> TYPE: DNA
<213> ORGANISM: artificial sequence
<220> FEATURE:
<223> OTHER INFORMATION: shRNA

<400> SEQUENCE: 28
gatccccagc tgggatcagc agagagttca agagactctc tgctgatccc agcttttttg         60
gaaa                                                                      64

<210> SEQ ID NO 29
<211> LENGTH: 64
<212> TYPE: DNA
<213> ORGANISM: artificial sequence
<220> FEATURE:
<223> OTHER INFORMATION: shRNA

<400> SEQUENCE: 29
agcttttcca aaaagctgg gatcagcaga gagtctcttg aactctctgc tgatcccagc          60
tggg                                                                      64

<210> SEQ ID NO 30
<211> LENGTH: 64
<212> TYPE: DNA
<213> ORGANISM: artificial sequence
```

```
<220> FEATURE:
<223> OTHER INFORMATION: shRNA

<400> SEQUENCE: 30
gatcccgcgc gaccttcgaa tgtaattcaa gagattacat tcgaaggtcg cgcttttttg     60
gaaa                                                                   64

<210> SEQ ID NO 31
<211> LENGTH: 64
<212> TYPE: DNA
<213> ORGANISM: artificial sequence
<220> FEATURE:
<223> OTHER INFORMATION: shRNA

<400> SEQUENCE: 31
agcttttcca aaaagcgcg accttcgaat gtaatctctt gaattacatt cgaaggtcgc      60
gcgg                                                                   64

<210> SEQ ID NO 32
<211> LENGTH: 64
<212> TYPE: DNA
<213> ORGANISM: artificial sequence
<220> FEATURE:
<223> OTHER INFORMATION: shRNA

<400> SEQUENCE: 32
gatcccgaga aggttgtccc gctttattca agagataaag cgggacaacc ttctttttg      60 gaaa                                                                   64

<210> SEQ ID NO 33
<211> LENGTH: 64
<212> TYPE: DNA
<213> ORGANISM: artificial sequence
<220> FEATURE:
<223> OTHER INFORMATION: shRNA

<400> SEQUENCE: 33
agcttttcca aaaagaagg ttgtcccgct ttatctcttg aataaagcgg gacaaccttc      60
tcgg                                                                   64

<210> SEQ ID NO 34
<211> LENGTH: 65
<212> TYPE: DNA
<213> ORGANISM: artificial sequence
<220> FEATURE:
<223> OTHER INFORMATION: shRNA

<400> SEQUENCE: 34
gatcccgcgc gaccttcgaa tgtaatttca agagaattac attcgaaggt cgcgtttttt     60
ggaaa                                                                  65

<210> SEQ ID NO 35
<211> LENGTH: 65
<212> TYPE: DNA
<213> ORGANISM: artificial sequence
<220> FEATURE:
<223> OTHER INFORMATION: shRNA

<400> SEQUENCE: 35
agcttttcca aaaacgcga ccttcgaatg taattctctt gaaattacat tcgaaggtcg      60
cgcgg                                                                  65
```

<210> SEQ ID NO 36
<211> LENGTH: 21
<212> TYPE: DNA
<213> ORGANISM: artificial sequence
<220> FEATURE:
<223> OTHER INFORMATION: siRNA

<400> SEQUENCE: 36
agaccagacc uaacagacat t                                              21

<210> SEQ ID NO 37
<211> LENGTH: 21
<212> TYPE: DNA
<213> ORGANISM: artificial sequence
<220> FEATURE:
<223> OTHER INFORMATION: siRNA

<400> SEQUENCE: 37
caucaguggu uggagaccat t                                              21

<210> SEQ ID NO 38
<211> LENGTH: 180
<212> TYPE: PRT
<213> ORGANISM: artificial sequence
<220> FEATURE:
<223> OTHER INFORMATION: RNF5 Mus musculus

<400> SEQUENCE: 38

Met Ala Ala Ala Glu Glu Asp Gly Gly Pro Glu Gly Pro Asn Arg
1               5                   10                  15

Glu Arg Gly Gly Ala Ser Ala Thr Phe Glu Cys Asn Ile Cys Leu Glu
            20                  25                  30

Thr Ala Arg Glu Ala Val Val Ser Val Cys Gly His Leu Tyr Cys Trp
        35                  40                  45

Pro Cys Leu His Gln Trp Leu Glu Thr Arg Pro Asp Arg Gln Glu Cys
    50                  55                  60

Pro Val Cys Lys Ala Gly Ile Ser Arg Glu Lys Val Val Pro Leu Tyr
65                  70                  75                  80

Gly Arg Gly Ser Gln Lys Pro Gln Asp Pro Arg Leu Lys Thr Pro Pro
                85                  90                  95

Arg Pro Gln Gly Gln Arg Pro Ala Pro Glu Ser Arg Gly Gly Phe Gln
            100                 105                 110

Pro Phe Gly Asp Ala Gly Gly Phe His Phe Ser Phe Gly Val Gly Ala
        115                 120                 125

Phe Pro Phe Gly Phe Phe Thr Thr Val Phe Asn Ala His Glu Pro Phe
    130                 135                 140

Arg Arg Gly Ala Gly Val Asp Leu Gly Gln Gly His Pro Ala Ser Ser
145                 150                 155                 160

Trp Gln Asp Ser Leu Phe Leu Phe Leu Ala Ile Phe Phe Phe Trp
                165                 170                 175

Leu Leu Ser Ile
            180

<210> SEQ ID NO 39
<211> LENGTH: 180
<212> TYPE: PRT
<213> ORGANISM: artificial sequence
<220> FEATURE:
<223> OTHER INFORMATION: RNF5 Homo sapiens

<400> SEQUENCE: 39

Met Ala Ala Ala Glu Glu Asp Gly Gly Pro Glu Gly Pro Asn Arg
1               5                   10                  15

Glu Arg Gly Gly Ala Gly Ala Thr Phe Glu Cys Asn Ile Cys Leu Glu
            20                  25                  30

Thr Ala Arg Glu Ala Val Val Ser Val Cys Gly His Leu Tyr Cys Trp
        35                  40                  45

Pro Cys Leu His Gln Trp Leu Glu Thr Arg Pro Glu Arg Gln Glu Cys
    50                  55                  60

Pro Val Cys Lys Ala Gly Ile Ser Arg Glu Lys Val Val Pro Leu Tyr
65                  70                  75                  80

Gly Arg Gly Ser Gln Lys Pro Gln Asp Pro Arg Leu Lys Thr Pro Pro
                85                  90                  95

Arg Pro Gln Gly Gln Arg Pro Ala Pro Glu Ser Arg Gly Gly Phe Gln
                100                 105                 110

Pro Phe Gly Asp Thr Gly Gly Phe His Phe Ser Phe Gly Val Gly Ala
            115                 120                 125

Phe Pro Phe Gly Phe Phe Thr Thr Val Phe Asn Ala His Glu Pro Phe
        130                 135                 140

Arg Arg Gly Thr Gly Val Asp Leu Gly Gln Gly His Pro Ala Ser Ser
145                 150                 155                 160

Trp Gln Asp Ser Leu Phe Leu Phe Leu Ala Ile Phe Phe Phe Phe Trp
                165                 170                 175

Leu Leu Ser Ile
            180

<210> SEQ ID NO 40
<211> LENGTH: 235
<212> TYPE: PRT
<213> ORGANISM: artificial sequence
<220> FEATURE:
<223> OTHER INFORMATION: RNF5 Caenorhabditis elegans

<400> SEQUENCE: 40

Met Ala Ser Glu Thr Lys Ala Pro Ser Glu Glu Pro Thr Ser Ser Ser
1               5                   10                  15

Asn Lys Asp Glu Ser Ala Arg Phe Glu Cys Asn Ile Cys Leu Asp Ala
            20                  25                  30

Ala Lys Asp Ala Val Val Ser Leu Cys Gly His Leu Phe Cys Trp Pro
        35                  40                  45

Cys Leu Ser Gln Trp Leu Asp Thr Arg Pro Asn Asn Gln Val Cys Pro
    50                  55                  60

Val Cys Lys Ser Ala Ile Asp Gly Asn Lys Val Val Pro Ile Tyr Gly
65                  70                  75                  80

Arg Gly Gly Asp Ser Ser Asp Pro Arg Lys Lys Val Pro Pro Arg Pro
                85                  90                  95

Lys Gly Gln Arg Ser Glu Pro Pro Gln Ser Phe Ala Gly Phe Asn
                100                 105                 110

Trp Gly Gly Asp Gly Gly Met Met Gly Gly Gly Gly Pro Asn Val His
            115                 120                 125

Phe Ser Phe Gly Ile Gly Thr Val Asn Gly Leu Phe Pro Leu Met Phe
        130                 135                 140

Met Leu Pro Phe Ile Gln Gly Ile Phe Pro Leu Ser Phe Val Ala Ser
145                 150                 155                 160

Phe Phe Gly Asn Gly Asn Gln Gly Ala Ala Ala Gly Gly Gly Asn
                165                 170                 175

Gly Gly Gly Asn Asp Gly Asn Asp Gly Thr His Ala His Thr His Gly
            180             185                 190

His Thr His Gly Pro Arg Gly His Gly Glu Ser Ala Ala Pro Gly Ser
        195                 200                 205

Arg Met Ala Gln Glu Glu Tyr Leu Ser Asn Ile Phe Lys Tyr Ile
    210                 215                 220

Gly Phe Phe Met Leu Phe Trp Leu Leu Phe Val
225                 230                 235

<210> SEQ ID NO 41
<211> LENGTH: 192
<212> TYPE: PRT
<213> ORGANISM: artificial sequence
<220> FEATURE:
<223> OTHER INFORMATION: RNF185 Homo sapiens

<400> SEQUENCE: 41

Met Ala Ser Lys Gly Pro Ser Ala Ser Ala Ser Pro Glu Asn Ser Ser
1               5                   10                  15

Ala Gly Gly Pro Ser Gly Ser Ser Asn Gly Ala Gly Glu Ser Gly Gly
            20                  25                  30

Gln Asp Ser Thr Phe Glu Cys Asn Ile Cys Leu Asp Thr Ala Lys Asp
        35                  40                  45

Ala Val Ile Ser Leu Cys Gly His Leu Phe Cys Trp Pro Cys Leu His
    50                  55                  60

Gln Trp Leu Glu Thr Arg Pro Asn Arg Gln Val Cys Pro Val Cys Lys
65                  70                  75                  80

Ala Gly Ile Ser Arg Asp Lys Val Ile Pro Leu Tyr Gly Arg Gly Ser
                85                  90                  95

Thr Gly Gln Gln Asp Pro Arg Glu Lys Thr Pro Pro Arg Pro Gln Gly
            100                 105                 110

Gln Arg Pro Glu Pro Glu Asn Arg Gly Gly Phe Gln Gly Phe Gly Phe
        115                 120                 125

Gly Asp Gly Gly Phe Gln Met Ser Phe Gly Ile Gly Ala Phe Pro Phe
    130                 135                 140

Gly Ile Phe Ala Thr Ala Phe Asn Ile Asn Asp Gly Arg Pro Pro Pro
145                 150                 155                 160

Ala Val Pro Gly Thr Pro Gln Tyr Val Asp Glu Gln Phe Leu Ser Arg
                165                 170                 175

Leu Phe Leu Phe Val Ala Leu Val Ile Met Phe Trp Leu Leu Ile Ala
            180                 185                 190

<210> SEQ ID NO 42
<211> LENGTH: 192
<212> TYPE: PRT
<213> ORGANISM: artificial sequence
<220> FEATURE:
<223> OTHER INFORMATION: RNF185 Mus musculus

<400> SEQUENCE: 42

Met Ala Ser Lys Gly Pro Ser Ala Ser Ala Ser Thr Glu Asn Ser Asn
1               5                   10                  15

Ala Gly Gly Pro Ser Gly Ser Ser Asn Gly Thr Gly Glu Ser Gly Gly
            20                  25                  30

Gln Asp Ser Thr Phe Glu Cys Asn Ile Cys Leu Asp Thr Ala Lys Asp
        35                  40                  45

Ala Val Ile Ser Leu Cys Gly His Leu Phe Cys Trp Pro Cys Leu His

```
            50                  55                  60
Gln Trp Leu Glu Thr Arg Pro Asn Arg Gln Val Cys Pro Val Cys Lys
 65                  70                  75                  80

Ala Gly Ile Ser Arg Asp Lys Val Ile Pro Leu Tyr Gly Arg Gly Ser
                 85                  90                  95

Thr Gly Gln Gln Asp Pro Arg Glu Lys Thr Pro Pro Arg Pro Gln Gly
                100                 105                 110

Gln Arg Pro Glu Pro Glu Asn Arg Gly Gly Phe Gln Gly Phe Gly Phe
            115                 120                 125

Gly Asp Gly Gly Phe Gln Met Ser Phe Gly Ile Gly Ala Phe Pro Phe
        130                 135                 140

Gly Ile Phe Ala Thr Ala Phe Asn Ile Asn Asp Gly Arg Pro Pro Pro
145                 150                 155                 160

Ala Val Pro Gly Thr Pro Gln Tyr Val Asp Glu Gln Phe Leu Ser Arg
                165                 170                 175

Leu Phe Leu Phe Val Ala Leu Val Ile Met Phe Trp Leu Leu Ile Ala
            180                 185                 190

<210> SEQ ID NO 43
<211> LENGTH: 21
<212> TYPE: DNA
<213> ORGANISM: artificial sequence
<220> FEATURE:
<223> OTHER INFORMATION: siRNA

<400> SEQUENCE: 43
cagacuuugu cauggagcut t                                       21

<210> SEQ ID NO 44
<211> LENGTH: 21
<212> TYPE: DNA
<213> ORGANISM: artificial sequence
<220> FEATURE:
<223> OTHER INFORMATION: siRNA

<400> SEQUENCE: 44
gucauguggu gccucuggut t                                       21

<210> SEQ ID NO 45
<211> LENGTH: 153
<212> TYPE: PRT
<213> ORGANISM: Artificial Sequence
<220> FEATURE:
<223> OTHER INFORMATION: consensus

<400> SEQUENCE: 45

Met Ala Ser Lys Gly Pro Ser Ala Ser Ala Ser Ala Glu Gly Gly Pro
 1               5                  10                  15

Gly Ser Ser Asn Gly Gly Glu Gly Gly Ala Thr Phe Glu Cys Asn Ile
                 20                  25                  30

Cys Leu Asp Thr Ala Lys Asp Ala Val Val Ser Leu Cys Gly His Leu
             35                  40                  45

Phe Cys Trp Pro Cys Leu His Gln Trp Leu Glu Thr Arg Pro Asn Arg
         50                  55                  60

Gln Val Cys Pro Val Cys Lys Ala Gly Ile Ser Arg Lys Val Val Pro
 65                  70                  75                  80

Leu Tyr Gly Arg Gly Ser Gln Asp Pro Arg Lys Thr Pro Pro Arg Pro
                 85                  90                  95

Gln Gly Gln Arg Pro Glu Pro Glu Arg Gly Gly Phe Gln Phe Gly Phe
```

```
                    100                 105                 110
Gly Asp Gly Gly Phe His Phe Ser Phe Gly Ile Gly Ala Phe Pro Phe
            115                 120                 125

Gly Phe Phe Ala Thr Phe Asn Ala Gly Val Pro Gly Glu Leu Ser Leu
    130                 135                 140

Phe Leu Phe Ala Phe Phe Trp Leu Leu
145                 150
```